(12) United States Patent
Kelly et al.

(10) Patent No.: US 10,736,690 B2
(45) Date of Patent: Aug. 11, 2020

(54) NEUROMODULATION CATHETERS AND ASSOCIATED SYSTEMS AND METHODS

(71) Applicant: Medtronic Ardian Luxembourg S.a.r.l., Luxembourg (LU)

(72) Inventors: Brian Kelly, Ballybrit (IE); Micheal Moriarty, Ballybrit (IE)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 319 days.

(21) Appl. No.: 14/691,389

(22) Filed: Apr. 20, 2015

(65) Prior Publication Data

US 2015/0305807 A1 Oct. 29, 2015

Related U.S. Application Data

(60) Provisional application No. 61/983,812, filed on Apr. 24, 2014.

(51) Int. Cl.
*A61B 18/14* (2006.01)
*A61B 18/00* (2006.01)

(52) U.S. Cl.
CPC ........... *A61B 18/1492* (2013.01); *A61B 2018/00178* (2013.01); *A61B 2018/00404* (2013.01); *A61B 2018/00434* (2013.01); *A61B 2018/00511* (2013.01); *A61B 2018/00577* (2013.01); *A61B 2018/00821* (2013.01); *A61B 2018/1435* (2013.01); *A61B 2018/1467* (2013.01)

(58) Field of Classification Search
CPC ...... A61B 18/1492; A61B 2018/00178; A61B 2018/00577; A61B 2018/00821; A61B 2018/1435; A61B 2018/1467; A61B 2562/0271
See application file for complete search history.

(56) References Cited

U.S. PATENT DOCUMENTS

| | | |
|---|---|---|
| 3,935,348 A | 1/1976 | Smith |
| 4,154,246 A | 5/1979 | LeVeen |

(Continued)

FOREIGN PATENT DOCUMENTS

| | | |
|---|---|---|
| CN | 2782017 | 5/2006 |
| CN | 201469401 | 5/2010 |

(Continued)

OTHER PUBLICATIONS

International Search Report and Written Opinion for International App. No. PCT/US2015/026711, dated Jul. 20, 2015, 13 pages.

(Continued)

*Primary Examiner* — Daniel W Fowler
*Assistant Examiner* — Tigist S Demie

(57) ABSTRACT

Methods for treating a patient using therapeutic renal neuromodulation and associated devices, systems, and methods are disclosed herein. One aspect of the present technology, for example, is directed to a catheter apparatus including an elongated shaft defined by a braid embedded within a polymer. The braid can include one or more thermocouple assemblies intertwined with a braiding element. The thermocouple assemblies can be coupled to one or more electrodes at a distal portion of the shaft.

13 Claims, 21 Drawing Sheets

(56) References Cited

U.S. PATENT DOCUMENTS

| | | |
|---|---|---|
| 4,169,464 A | 10/1979 | Obrez |
| 4,419,819 A | 12/1983 | Dickhudt et al. |
| 4,602,624 A | 7/1986 | Naples et al. |
| 4,649,936 A | 3/1987 | Ungar et al. |
| 4,660,571 A | 4/1987 | Hess et al. |
| 4,706,671 A | 11/1987 | Weinrib |
| 4,709,698 A | 12/1987 | Johnston et al. |
| 4,764,504 A | 8/1988 | Johnson et al. |
| 4,781,682 A | 11/1988 | Patel |
| 4,796,643 A | 1/1989 | Nakazawa et al. |
| 4,819,661 A | 4/1989 | Heil, Jr. et al. |
| 4,834,724 A | 5/1989 | Geiss et al. |
| 4,860,769 A | 8/1989 | Fogarty et al. |
| 4,890,623 A | 1/1990 | Cook et al. |
| 4,920,979 A | 5/1990 | Bullara |
| 4,921,484 A | 5/1990 | Hillstead |
| 4,957,118 A | 9/1990 | Erlebacher |
| 4,961,377 A | 10/1990 | Bando et al. |
| 4,976,711 A | 12/1990 | Parins et al. |
| 4,995,868 A | 2/1991 | Brazier |
| 4,998,923 A | 3/1991 | Samson et al. |
| 5,002,067 A | 3/1991 | Berthelsen et al. |
| 5,011,488 A | 4/1991 | Ginsburg |
| 5,016,808 A | 5/1991 | Heil, Jr. et al. |
| 5,052,998 A | 10/1991 | Zimmon |
| 5,054,501 A | 10/1991 | Chuttani et al. |
| 5,071,407 A | 12/1991 | Termin et al. |
| 5,071,424 A | 12/1991 | Reger |
| 5,133,365 A | 7/1992 | Heil, Jr. et al. |
| 5,156,151 A | 10/1992 | Imran |
| 5,156,610 A | 10/1992 | Reger |
| 5,158,564 A | 10/1992 | Schnepp-Pesch et al. |
| 5,163,928 A | 11/1992 | Hobbs et al. |
| 5,188,602 A | 2/1993 | Nichols |
| 5,188,619 A | 2/1993 | Myers |
| 5,209,723 A | 5/1993 | Twardowski et al. |
| 5,211,651 A | 5/1993 | Reger et al. |
| 5,228,442 A | 7/1993 | Imran |
| 5,239,999 A | 8/1993 | Imran |
| 5,249,585 A | 10/1993 | Turner et al. |
| 5,263,492 A | 11/1993 | Voyce |
| 5,263,493 A | 11/1993 | Avitall |
| 5,279,299 A | 1/1994 | Imran |
| 5,282,484 A | 2/1994 | Reger |
| 5,296,510 A | 3/1994 | Yamada et al. |
| 5,300,068 A | 4/1994 | Rosar et al. |
| 5,300,099 A | 4/1994 | Rudie |
| 5,308,323 A | 5/1994 | Sogawa et al. |
| 5,318,525 A | 6/1994 | West et al. |
| 5,322,064 A | 6/1994 | Lundquist |
| 5,324,284 A | 6/1994 | Imran |
| 5,327,905 A | 7/1994 | Avitall |
| 5,330,496 A | 7/1994 | Alferness |
| 5,345,031 A | 9/1994 | Schwartz et al. |
| 5,345,936 A | 9/1994 | Pomeranz et al. |
| 5,354,297 A | 10/1994 | Avitall |
| 5,358,514 A | 10/1994 | Schulman et al. |
| 5,365,926 A | 11/1994 | Desai |
| 5,368,591 A | 11/1994 | Lennox et al. |
| 5,368,592 A | 11/1994 | Stern et al. |
| 5,383,856 A | 1/1995 | Bersin |
| 5,387,233 A | 2/1995 | Alferness et al. |
| 5,397,304 A | 3/1995 | Truckai |
| 5,397,339 A | 3/1995 | Desai |
| 5,399,164 A | 3/1995 | Snoke et al. |
| 5,405,374 A | 4/1995 | Stein |
| 5,411,546 A | 5/1995 | Bowald et al. |
| 5,423,744 A | 6/1995 | Gencheff et al. |
| 5,425,364 A | 6/1995 | Imran |
| 5,427,118 A | 6/1995 | Nita et al. |
| 5,441,483 A | 8/1995 | Avitall |
| 5,445,148 A | 8/1995 | Jaraczewski et al. |
| 5,454,786 A | 10/1995 | Walker et al. |
| 5,456,680 A * | 10/1995 | Taylor ............... A61B 18/245 606/15 |
| 5,462,545 A | 10/1995 | Wang et al. |
| 5,476,495 A | 12/1995 | Kordis et al. |
| 5,476,498 A | 12/1995 | Ayers |
| 5,477,856 A | 12/1995 | Lundquist |
| 5,482,037 A | 1/1996 | Borghi |
| 5,484,400 A | 1/1996 | Edwards et al. |
| 5,487,385 A | 1/1996 | Avitall |
| 5,487,757 A | 1/1996 | Truckai et al. |
| 5,497,774 A | 3/1996 | Swartz et al. |
| 5,505,201 A | 4/1996 | Grill, Jr. et al. |
| 5,507,743 A | 4/1996 | Edwards et al. |
| 5,509,909 A | 4/1996 | Moy |
| 5,523,092 A | 6/1996 | Hanson et al. |
| 5,529,820 A | 6/1996 | Nomi et al. |
| 5,545,193 A | 8/1996 | Fleischman et al. |
| 5,545,200 A | 8/1996 | West et al. |
| 5,545,475 A | 8/1996 | Korleski |
| 5,549,661 A | 8/1996 | Kordis et al. |
| 5,554,114 A | 9/1996 | Wallace et al. |
| 5,558,643 A | 9/1996 | Samson et al. |
| 5,564,440 A | 10/1996 | Swartz et al. |
| 5,571,147 A | 11/1996 | Sluijter et al. |
| 5,575,766 A | 11/1996 | Swartz et al. |
| 5,575,810 A | 11/1996 | Swanson et al. |
| 5,582,609 A | 12/1996 | Swanson et al. |
| 5,588,964 A | 12/1996 | Imran et al. |
| 5,591,132 A | 1/1997 | Carrie |
| 5,599,345 A | 2/1997 | Edwards et al. |
| 5,609,151 A | 3/1997 | Mulier et al. |
| 5,617,854 A | 4/1997 | Munsif |
| 5,626,576 A | 5/1997 | Janssen |
| 5,628,775 A | 5/1997 | Jackson et al. |
| 5,636,634 A | 6/1997 | Kordis et al. |
| 5,637,090 A | 6/1997 | McGee et al. |
| 5,642,736 A | 7/1997 | Avitall |
| 5,653,684 A | 8/1997 | Laptewicz et al. |
| 5,672,174 A | 9/1997 | Gough et al. |
| 5,676,662 A | 10/1997 | Fleischhacker et al. |
| 5,678,296 A | 10/1997 | Fleischhacker et al. |
| 5,680,860 A | 10/1997 | Imran |
| 5,681,280 A | 10/1997 | Rusk et al. |
| 5,687,723 A | 11/1997 | Avitall |
| 5,688,266 A | 11/1997 | Edwards et al. |
| 5,690,611 A | 11/1997 | Swartz et al. |
| 5,693,082 A | 12/1997 | Warner et al. |
| 5,695,506 A | 12/1997 | Pike et al. |
| 5,697,928 A | 12/1997 | Walcott et al. |
| 5,700,282 A | 12/1997 | Zabara |
| 5,707,400 A | 1/1998 | Terry, Jr. et al. |
| 5,709,874 A | 1/1998 | Hanson et al. |
| 5,715,818 A | 2/1998 | Swartz et al. |
| 5,716,410 A | 2/1998 | Wang et al. |
| 5,722,401 A | 3/1998 | Pietroski et al. |
| 5,725,512 A | 3/1998 | Swartz et al. |
| 5,727,555 A | 3/1998 | Chait |
| 5,730,127 A | 3/1998 | Avitall |
| 5,730,741 A | 3/1998 | Horzewski et al. |
| 5,741,429 A | 4/1998 | Donadio, III et al. |
| 5,743,903 A | 4/1998 | Stern et al. |
| 5,755,760 A | 5/1998 | Maguire et al. |
| 5,755,761 A | 5/1998 | Obino |
| 5,772,590 A | 6/1998 | Webster, Jr. |
| 5,800,494 A | 9/1998 | Campbell et al. |
| 5,807,249 A | 9/1998 | Qin et al. |
| 5,807,395 A | 9/1998 | Muller et al. |
| 5,810,802 A | 9/1998 | Panescu et al. |
| 5,814,028 A | 9/1998 | Swartz et al. |
| 5,823,955 A | 10/1998 | Kuck et al. |
| 5,824,026 A * | 10/1998 | Diaz ............... A61B 18/1492 607/116 |
| 5,827,242 A | 10/1998 | Follmer et al. |
| 5,827,268 A | 10/1998 | Laufer |
| 5,827,272 A | 10/1998 | Breining et al. |
| 5,842,984 A | 12/1998 | Avitall |
| 5,846,355 A | 12/1998 | Spencer et al. |
| 5,860,920 A | 1/1999 | McGee et al. |
| 5,860,974 A | 1/1999 | Abele |
| 5,865,787 A | 2/1999 | Shapland et al. |
| 5,865,815 A | 2/1999 | Tihon |

(56) References Cited

U.S. PATENT DOCUMENTS

| | | |
|---|---|---|
| 5,871,444 A | 2/1999 | Ouchi |
| 5,871,523 A | 2/1999 | Fleischman et al. |
| 5,871,531 A | 2/1999 | Struble |
| 5,873,865 A | 2/1999 | Horzewski et al. |
| 5,879,295 A | 3/1999 | Li et al. |
| 5,882,333 A | 3/1999 | Schaer et al. |
| 5,882,346 A | 3/1999 | Pomeranz et al. |
| 5,891,114 A | 4/1999 | Chien et al. |
| 5,893,885 A | 4/1999 | Webster et al. |
| 5,895,378 A | 4/1999 | Berenstein et al. |
| 5,904,667 A | 5/1999 | Falwell |
| 5,910,129 A | 6/1999 | Koblish et al. |
| 5,916,214 A | 6/1999 | Cosio et al. |
| 5,931,830 A | 8/1999 | Jacobsen et al. |
| 5,931,848 A | 8/1999 | Saadat |
| 5,935,102 A | 8/1999 | Bowden et al. |
| 5,935,124 A | 8/1999 | Klumb et al. |
| 5,938,694 A | 8/1999 | Jaraczewski et al. |
| 5,941,823 A | 8/1999 | Chait |
| 5,944,710 A | 8/1999 | Dev et al. |
| 5,951,471 A | 9/1999 | de la Rama et al. |
| 5,951,494 A | 9/1999 | Wang et al. |
| 5,951,539 A | 9/1999 | Nita et al. |
| 5,954,719 A | 9/1999 | Chen et al. |
| 5,957,961 A | 9/1999 | Maguire et al. |
| 5,961,511 A | 10/1999 | Mortier et al. |
| 5,967,978 A | 10/1999 | Littmann et al. |
| 5,968,085 A | 10/1999 | Morris et al. |
| 5,971,975 A | 10/1999 | Mills et al. |
| 5,972,019 A | 10/1999 | Engelson et al. |
| 5,972,026 A | 10/1999 | Laufer et al. |
| 5,980,516 A | 11/1999 | Mulier et al. |
| 5,980,563 A | 11/1999 | Tu et al. |
| 5,983,141 A | 11/1999 | Sluijter et al. |
| 5,987,344 A | 11/1999 | West |
| 5,993,462 A | 11/1999 | Pomeranz et al. |
| 5,997,526 A | 12/1999 | Giba et al. |
| 6,004,269 A | 12/1999 | Crowley et al. |
| 6,004,316 A | 12/1999 | Laufer |
| 6,004,348 A | 12/1999 | Banas et al. |
| 6,009,877 A | 1/2000 | Edwards |
| 6,012,457 A | 1/2000 | Lesh |
| 6,024,740 A | 2/2000 | Lesh et al. |
| 6,032,077 A | 2/2000 | Pomeranz |
| 6,036,687 A | 3/2000 | Laufer et al. |
| 6,042,578 A | 3/2000 | Dinh et al. |
| 6,048,329 A | 4/2000 | Thompson et al. |
| 6,048,338 A | 4/2000 | Larson et al. |
| 6,064,902 A | 5/2000 | Haissaguerre et al. |
| 6,066,134 A | 5/2000 | Eggers et al. |
| 6,071,729 A | 6/2000 | Jeffries et al. |
| 6,074,339 A | 6/2000 | Gambale et al. |
| 6,074,361 A | 6/2000 | Jacobs |
| 6,074,378 A | 6/2000 | Mouri et al. |
| 6,076,012 A | 6/2000 | Swanson et al. |
| 6,078,830 A * | 6/2000 | Levin ............... A61B 18/1492 600/374 |
| 6,078,840 A | 6/2000 | Stokes |
| 6,078,841 A | 6/2000 | Kuzma |
| 6,079,414 A | 6/2000 | Roth |
| 6,080,171 A | 6/2000 | Keith et al. |
| 6,090,104 A | 7/2000 | Webster, Jr. |
| 6,091,995 A | 7/2000 | Ingle et al. |
| 6,094,596 A | 7/2000 | Morgan |
| 6,096,036 A | 8/2000 | Bowe et al. |
| 6,099,524 A | 8/2000 | Lipson et al. |
| 6,102,890 A | 8/2000 | Stivland et al. |
| 6,106,522 A | 8/2000 | Fleischman et al. |
| 6,110,187 A | 8/2000 | Donlon |
| 6,117,101 A | 9/2000 | Diederich et al. |
| 6,125,302 A | 9/2000 | Kuzma |
| 6,129,724 A | 10/2000 | Fleischman et al. |
| 6,129,750 A | 10/2000 | Tockman et al. |
| 6,132,456 A | 10/2000 | Sommer et al. |
| 6,135,999 A | 10/2000 | Fanton et al. |
| 6,142,993 A | 11/2000 | Whayne et al. |
| 6,146,381 A | 11/2000 | Bowe et al. |
| 6,149,620 A | 11/2000 | Baker et al. |
| 6,152,912 A | 11/2000 | Jansen et al. |
| 6,156,046 A | 12/2000 | Passafaro et al. |
| 6,159,187 A | 12/2000 | Park et al. |
| 6,161,048 A | 12/2000 | Sluijter et al. |
| 6,161,049 A | 12/2000 | Rudie et al. |
| 6,164,283 A | 12/2000 | Lesh |
| 6,165,163 A | 12/2000 | Chien et al. |
| 6,190,356 B1 | 2/2001 | Bersin |
| 6,210,362 B1 | 4/2001 | Ponzi |
| 6,210,406 B1 | 4/2001 | Webster |
| 6,213,995 B1 | 4/2001 | Steen et al. |
| 6,214,002 B1 | 4/2001 | Fleischman et al. |
| 6,219,577 B1 | 4/2001 | Brown, III et al. |
| 6,223,070 B1 | 4/2001 | Chait |
| 6,224,592 B1 | 5/2001 | Eggers et al. |
| 6,228,109 B1 | 5/2001 | Tu et al. |
| 6,245,020 B1 | 6/2001 | Moore et al. |
| 6,245,045 B1 | 6/2001 | Stratieriko |
| 6,246,912 B1 | 6/2001 | Sluijter et al. |
| 6,246,914 B1 | 6/2001 | de la Rama et al. |
| 6,254,588 B1 | 7/2001 | Jones et al. |
| 6,263,224 B1 | 7/2001 | West |
| 6,270,496 B1 | 8/2001 | Bowe et al. |
| 6,273,876 B1 | 8/2001 | Klima et al. |
| 6,273,886 B1 | 8/2001 | Edwards et al. |
| 6,280,441 B1 | 8/2001 | Ryan |
| 6,283,951 B1 | 9/2001 | Flaherty et al. |
| 6,283,960 B1 | 9/2001 | Ashley |
| 6,287,301 B1 | 9/2001 | Thompson et al. |
| 6,292,695 B1 | 9/2001 | Webster, Jr. et al. |
| 6,293,943 B1 | 9/2001 | Panescu et al. |
| 6,293,256 B1 | 10/2001 | Meyer |
| 6,299,623 B1 | 10/2001 | Wulfrnan |
| 6,308,090 B1 | 10/2001 | Tu et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,325,797 B1 | 12/2001 | Stewart et al. |
| 6,346,074 B1 | 2/2002 | Roth |
| 6,364,904 B1 | 4/2002 | Smith |
| 6,371,965 B2 | 4/2002 | Gifford, III et al. |
| 6,385,472 B1 | 5/2002 | Hall et al. |
| 6,387,105 B1 | 5/2002 | Gifford, III et al. |
| 6,401,720 B1 | 6/2002 | Stevens et al. |
| 6,405,732 B1 | 6/2002 | Edwards et al. |
| 6,409,742 B1 | 6/2002 | Fulton, III et al. |
| 6,413,255 B1 | 7/2002 | Stern |
| 6,427,089 B1 | 7/2002 | Knowlton |
| 6,430,426 B2 | 8/2002 | Avitall |
| 6,436,056 B1 | 8/2002 | Wang et al. |
| 6,442,415 B1 | 8/2002 | Bis et al. |
| 6,443,965 B1 | 9/2002 | Gifford, III et al. |
| 6,451,034 B1 | 9/2002 | Gifford, III et al. |
| 6,451,045 B1 | 9/2002 | Walker et al. |
| 6,454,775 B1 | 9/2002 | Demarais et al. |
| 6,480,747 B2 | 11/2002 | Schmidt |
| 6,482,202 B1 | 11/2002 | Goble et al. |
| 6,488,679 B1 | 12/2002 | Swanson et al. |
| 6,491,705 B2 | 12/2002 | Gifford, III et al. |
| 6,496,737 B2 | 12/2002 | Rudie et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,506,189 B1 | 1/2003 | Rittman, III et al. |
| 6,508,804 B2 | 1/2003 | Sarge et al. |
| 6,511,492 B1 | 1/2003 | Rosenbluth et al. |
| 6,514,226 B1 | 2/2003 | Levin et al. |
| 6,514,236 B1 | 2/2003 | Stratienko |
| 6,514,249 B1 | 2/2003 | Maguire et al. |
| 6,517,572 B2 | 2/2003 | Kugler et al. |
| 6,522,926 B1 | 2/2003 | Kieval et al. |
| 6,527,739 B1 | 3/2003 | Bigus et al. |
| 6,529,756 B1 | 3/2003 | Phan et al. |
| 6,530,935 B2 | 3/2003 | Wensel et al. |
| 6,540,734 B1 | 4/2003 | Chiu et al. |
| 6,542,781 B1 | 4/2003 | Koblish et al. |

(56) References Cited

U.S. PATENT DOCUMENTS

| | | | |
|---|---|---|---|
| 6,546,272 B1 | 4/2003 | MacKinnon et al. | |
| 6,546,280 B2 | 4/2003 | Osborne | |
| 6,549,800 B1 | 4/2003 | Atalar et al. | |
| 6,554,827 B2 | 4/2003 | Chandrasekaran et al. | |
| 6,562,031 B2 | 5/2003 | Chandrasekaran et al. | |
| 6,562,034 B2 | 5/2003 | Edwards et al. | |
| 6,564,096 B2 | 5/2003 | Mest | |
| 6,565,582 B2 | 5/2003 | Gifford, III et al. | |
| 6,569,177 B1 | 5/2003 | Dillard et al. | |
| 6,572,612 B2 | 6/2003 | Stewart et al. | |
| 6,585,718 B2 | 7/2003 | Hayzelden et al. | |
| 6,592,581 B2 | 7/2003 | Bowe | |
| 6,602,242 B1 | 8/2003 | Fung et al. | |
| 6,605,061 B2 | 8/2003 | VanTassel et al. | |
| 6,607,520 B2 | 8/2003 | Keane | |
| 6,610,046 B1 | 8/2003 | Usami et al. | |
| 6,610,083 B2 | 8/2003 | Keller et al. | |
| 6,611,720 B2 | 8/2003 | Hata et al. | |
| 6,613,046 B1 | 9/2003 | Jenkins et al. | |
| 6,616,624 B1 | 9/2003 | Kieval | |
| 6,622,731 B2 | 9/2003 | Daniel et al. | |
| 6,623,515 B2 | 9/2003 | Mulier et al. | |
| 6,628,976 B1 | 9/2003 | Fuimaono et al. | |
| 6,632,193 B1 | 10/2003 | Davison et al. | |
| 6,635,054 B2 | 10/2003 | Fjield et al. | |
| 6,640,120 B1 | 10/2003 | Swanson et al. | |
| 6,648,854 B1 | 11/2003 | Patterson et al. | |
| 6,651,672 B2 | 11/2003 | Roth | |
| 6,652,517 B1 | 11/2003 | Hall et al. | |
| 6,656,195 B2 | 12/2003 | Peters et al. | |
| 6,659,981 B2 | 12/2003 | Stewart et al. | |
| 6,669,670 B1 | 12/2003 | Muni et al. | |
| 6,669,692 B1 | 12/2003 | Nelson et al. | |
| 6,676,678 B2 | 1/2004 | Gifford, III et al. | |
| 6,679,268 B2 | 1/2004 | Stevens et al. | |
| 6,682,541 B1 | 1/2004 | Gifford, III et al. | |
| 6,685,648 B2 | 2/2004 | Flaherty et al. | |
| 6,692,490 B1 | 2/2004 | Edwards | |
| 6,695,857 B2 | 2/2004 | Gifford, III et al. | |
| 6,699,257 B2 | 3/2004 | Gifford, III et al. | |
| 6,702,811 B2 | 3/2004 | Stewart et al. | |
| 6,706,010 B1 | 3/2004 | Miki et al. | |
| 6,711,444 B2 | 3/2004 | Koblish | |
| 6,716,207 B2 | 4/2004 | Farnholtz | |
| 6,723,043 B2 | 4/2004 | Kleeman et al. | |
| 6,736,835 B2 | 5/2004 | Pellegrino et al. | |
| 6,745,080 B2 | 6/2004 | Koblish | |
| 6,746,446 B1 * | 6/2004 | Hill | A61B 18/1492 604/95.04 |
| 6,746,474 B2 | 6/2004 | Saadat | |
| 6,749,560 B1 | 6/2004 | Konstorum et al. | |
| 6,752,805 B2 | 6/2004 | Maguire et al. | |
| 6,758,830 B1 | 7/2004 | Schaer et al. | |
| 6,770,070 B1 | 8/2004 | Balbierz | |
| 6,773,433 B2 | 8/2004 | Stewart et al. | |
| 6,780,183 B2 | 8/2004 | Jimenez, Jr. et al. | |
| 6,790,206 B2 | 9/2004 | Paneseu | |
| 6,802,840 B2 | 10/2004 | Chin et al. | |
| 6,802,857 B1 | 10/2004 | Walsh et al. | |
| 6,814,733 B2 | 11/2004 | Schwartz et al. | |
| 6,817,999 B2 | 11/2004 | Berube et al. | |
| 6,829,497 B2 | 12/2004 | Mogul | |
| 6,830,568 B1 | 12/2004 | Kesten et al. | |
| 6,845,267 B2 | 1/2005 | Harrison et al. | |
| 6,847,848 B2 | 1/2005 | Sterzer et al. | |
| 6,849,075 B2 | 2/2005 | Bertolero et al. | |
| 6,850,801 B2 | 2/2005 | Kieval et al. | |
| 6,869,431 B2 | 3/2005 | Maguire et al. | |
| 6,882,886 B1 | 4/2005 | Witte et al. | |
| 6,884,260 B2 | 4/2005 | Kugler et al. | |
| 6,885,888 B2 | 4/2005 | Rezai | |
| 6,889,694 B2 | 5/2005 | Hooven | |
| 6,890,329 B2 | 5/2005 | Carroll et al. | |
| 6,893,436 B2 | 5/2005 | Woodard et al. | |
| 6,893,438 B2 | 5/2005 | Hall et al. | |
| 6,899,711 B2 | 5/2005 | Stewart et al. | |
| 6,905,510 B2 | 6/2005 | Saab | |
| 6,909,009 B2 | 6/2005 | Korithe | |
| 6,909,920 B2 | 6/2005 | Lokhoff et al. | |
| 6,915,806 B2 | 7/2005 | Pacek et al. | |
| 6,917,834 B2 | 7/2005 | Koblish et al. | |
| 6,923,808 B2 | 8/2005 | Taimisto | |
| 6,926,669 B1 | 8/2005 | Stewart et al. | |
| 6,926,713 B2 | 8/2005 | Rioux et al. | |
| 6,939,346 B2 | 9/2005 | Kannenberg et al. | |
| 6,941,953 B2 | 9/2005 | Feld et al. | |
| 6,945,956 B2 | 9/2005 | Waldhauser et al. | |
| 6,949,097 B2 | 9/2005 | Stewart et al. | |
| 6,952,615 B2 | 10/2005 | Satake | |
| 6,955,175 B2 | 10/2005 | Stevens et al. | |
| 6,960,206 B2 | 11/2005 | Keane | |
| 6,960,207 B2 | 11/2005 | Vanney et al. | |
| 6,966,908 B2 | 11/2005 | Maguire et al. | |
| 6,972,016 B2 | 12/2005 | Hill, III et al. | |
| 6,984,238 B2 | 1/2006 | Gifford, III et al. | |
| 7,013,169 B2 | 3/2006 | Bowe | |
| 7,013,170 B2 | 3/2006 | Bowe | |
| 7,058,456 B2 | 6/2006 | Pierce | |
| 7,063,719 B2 | 6/2006 | Jansen et al. | |
| 7,081,115 B2 | 7/2006 | Taimisto | |
| 7,087,051 B2 | 8/2006 | Bourne et al. | |
| 7,100,614 B2 | 9/2006 | Stevens et al. | |
| 7,102,151 B2 | 9/2006 | Reinberg et al. | |
| 7,104,988 B2 | 9/2006 | Altman et al. | |
| 7,110,828 B2 | 9/2006 | Kolberg et al. | |
| 7,112,211 B2 | 9/2006 | Gifford, III et al. | |
| 7,115,134 B2 | 10/2006 | Chambers | |
| 7,115,183 B2 | 10/2006 | Larson et al. | |
| 7,137,990 B2 | 11/2006 | Hebert et al. | |
| 7,149,574 B2 | 12/2006 | Yun et al. | |
| 7,153,315 B2 | 12/2006 | Miller | |
| 7,155,271 B2 | 12/2006 | Halperin et al. | |
| 7,158,832 B2 | 1/2007 | Kieval et al. | |
| 7,162,303 B2 | 1/2007 | Levin et al. | |
| 7,172,610 B2 | 2/2007 | Heitzmann et al. | |
| 7,184,811 B2 | 2/2007 | Phan et al. | |
| 7,192,427 B2 | 3/2007 | Chapelon et al. | |
| 7,201,738 B1 | 4/2007 | Bengmark | |
| 7,211,082 B2 | 5/2007 | Hall et al. | |
| 7,221,979 B2 | 5/2007 | Zhou et al. | |
| 7,232,458 B2 | 6/2007 | Saadat | |
| 7,233,184 B1 | 7/2007 | Megerman et al. | |
| 7,241,273 B2 | 7/2007 | Maguire et al. | |
| 7,254,451 B2 | 8/2007 | Seifert et al. | |
| 7,264,619 B2 | 9/2007 | Venturelli | |
| 7,276,062 B2 | 10/2007 | McDaniel et al. | |
| 7,282,213 B2 | 10/2007 | Schroeder et al. | |
| 7,285,119 B2 | 10/2007 | Stewart et al. | |
| 7,291,146 B2 | 11/2007 | Steinke et al. | |
| 7,294,127 B2 | 11/2007 | Leung et al. | |
| 7,311,705 B2 | 12/2007 | Sra | |
| 7,338,467 B2 | 3/2008 | Lutter | |
| 7,367,972 B2 | 5/2008 | Francischelli et al. | |
| 7,381,200 B2 | 6/2008 | Katoh et al. | |
| 7,390,894 B2 | 6/2008 | Weinshilboum et al. | |
| 7,393,338 B2 | 7/2008 | Nita | |
| 7,402,151 B2 | 7/2008 | Rosenman et al. | |
| 7,404,824 B1 | 7/2008 | Webler et al. | |
| 7,435,248 B2 | 10/2008 | Taimisto et al. | |
| 7,486,805 B2 | 2/2009 | Krattiger | |
| 7,488,338 B2 | 2/2009 | Eidenschink | |
| 7,494,486 B2 | 2/2009 | Mische et al. | |
| 7,494,488 B2 | 2/2009 | Weber et al. | |
| 7,497,858 B2 | 3/2009 | Chapelon et al. | |
| 7,517,349 B2 | 4/2009 | Truckai et al. | |
| 7,520,863 B2 | 4/2009 | Grewe et al. | |
| 7,526,343 B2 | 4/2009 | Peterson et al. | |
| 7,540,865 B2 | 6/2009 | Griffin et al. | |
| 7,542,808 B1 | 6/2009 | Peterson et al. | |
| 7,563,247 B2 | 7/2009 | Maguire et al. | |
| 7,597,704 B2 | 10/2009 | Frazier et al. | |
| 7,617,005 B2 | 11/2009 | Demarais et al. | |
| 7,620,451 B2 | 11/2009 | Demarais et al. | |
| 7,637,903 B2 | 12/2009 | Lentz et al. | |

(56) References Cited

U.S. PATENT DOCUMENTS

| | | |
|---|---|---|
| 7,646,544 B2 | 1/2010 | Batchko et al. |
| 7,647,115 B2 | 1/2010 | Levin et al. |
| 7,647,124 B2 | 1/2010 | Williams |
| 7,653,438 B2 | 1/2010 | Deem et al. |
| 7,670,335 B2 | 3/2010 | Keidar |
| 7,682,319 B2 | 3/2010 | Martin et al. |
| 7,699,809 B2 | 4/2010 | Urmey |
| 7,706,894 B2 | 4/2010 | Stewart et al. |
| 7,708,704 B2 | 5/2010 | Mitelberg et al. |
| 7,717,853 B2 | 5/2010 | Nita |
| 7,717,948 B2 | 5/2010 | Demarais et al. |
| 7,727,178 B2 | 6/2010 | Wilson et al. |
| 7,727,187 B2 | 6/2010 | Lentz |
| 7,729,782 B2 | 6/2010 | Williams et al. |
| 7,747,334 B2 | 6/2010 | Bly et al. |
| 7,758,520 B2 | 7/2010 | Griffin et al. |
| 7,763,012 B2 | 7/2010 | Petrick et al. |
| 7,771,410 B2 | 8/2010 | Venturelli |
| 7,771,421 B2 | 8/2010 | Stewart et al. |
| 7,778,703 B2 | 8/2010 | Gross et al. |
| 7,780,660 B2 | 8/2010 | Bourne et al. |
| 7,785,289 B2 | 8/2010 | Rios et al. |
| 7,789,877 B2 | 9/2010 | Vanney |
| 7,806,871 B2 | 10/2010 | Li et al. |
| 7,811,265 B2 | 10/2010 | Hering et al. |
| 7,811,281 B1 | 10/2010 | Rentrop |
| 7,815,637 B2 | 10/2010 | Ormsby et al. |
| 7,819,866 B2 | 10/2010 | Bednarek |
| 7,846,157 B2 | 12/2010 | Kozel |
| 7,850,685 B2 | 12/2010 | Kunis et al. |
| 7,862,565 B2 | 1/2011 | Eder et al. |
| 7,863,897 B2 | 1/2011 | Slocum, Jr. et al. |
| 7,867,219 B2 | 1/2011 | Chambers |
| 7,881,807 B2 | 2/2011 | Schaer |
| 7,890,188 B2 | 2/2011 | Zhang et al. |
| 7,896,873 B2 | 3/2011 | Hiller et al. |
| 7,905,862 B2 | 3/2011 | Sampson |
| 7,927,370 B2 | 4/2011 | Webler et al. |
| 7,937,160 B2 | 5/2011 | Garabedian et al. |
| 7,938,830 B2 | 5/2011 | Saadat et al. |
| 7,942,928 B2 | 5/2011 | Webler et al. |
| 7,959,630 B2 | 6/2011 | Taimisto et al. |
| 7,967,816 B2 | 6/2011 | Ocel et al. |
| 7,989,042 B2 | 8/2011 | Obara et al. |
| 8,007,440 B2 | 8/2011 | Magnin et al. |
| 8,007,462 B2 | 8/2011 | Gibson et al. |
| 8,019,435 B2 | 9/2011 | Hastings et al. |
| 8,027,718 B2 | 9/2011 | Spinner et al. |
| 8,043,288 B2 | 10/2011 | Dando et al. |
| 8,062,284 B2 | 11/2011 | Booth |
| 8,075,580 B2 | 12/2011 | Makower |
| 8,088,127 B2 | 1/2012 | Mayse et al. |
| 8,092,444 B2 | 1/2012 | Lentz et al. |
| 8,100,859 B2 | 1/2012 | Patterson et al. |
| 8,123,739 B2 | 2/2012 | McQueen et al. |
| 8,124,876 B2 | 2/2012 | Dayton et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,172,829 B2 | 5/2012 | Farnholtz |
| 8,175,711 B2 | 5/2012 | Demarais et al. |
| 8,190,238 B2 | 5/2012 | Moll et al. |
| 8,192,428 B2 | 6/2012 | Truckai et al. |
| 8,241,217 B2 | 8/2012 | Chiang et al. |
| 8,251,977 B2 | 8/2012 | Partlett |
| 8,257,351 B2 | 9/2012 | Stewart et al. |
| 8,292,881 B2 | 10/2012 | Brannan et al. |
| 8,308,722 B2 | 11/2012 | Ormsby et al. |
| 8,337,492 B2 | 12/2012 | Kunis et al. |
| 8,343,145 B2 | 1/2013 | Brannan |
| 8,376,865 B2 | 2/2013 | Forster et al. |
| 8,380,275 B2 | 2/2013 | Kim et al. |
| 8,388,680 B2 | 3/2013 | Starksen et al. |
| 8,398,629 B2 | 3/2013 | Thistle |
| 8,401,650 B2 | 3/2013 | Simon et al. |
| 8,409,193 B2 | 4/2013 | Young et al. |
| 8,409,195 B2 | 4/2013 | Young |
| 8,418,362 B2 | 4/2013 | Zerfas et al. |
| 8,473,023 B2 | 6/2013 | Worley et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,571,665 B2 | 10/2013 | Moffitt et al. |
| 8,740,849 B1 | 6/2014 | Fischell et al. |
| 8,909,316 B2 | 12/2014 | Ng |
| 8,974,451 B2 | 3/2015 | Smith |
| 9,014,821 B2 | 4/2015 | Wang |
| 9,050,106 B2 | 6/2015 | Hill et al. |
| 9,055,956 B2 | 6/2015 | McRae et al. |
| 9,084,609 B2 | 7/2015 | Smith |
| 9,162,046 B2 | 10/2015 | Hill et al. |
| 9,192,435 B2 | 11/2015 | Jenson |
| 9,333,113 B2 | 5/2016 | Abunassar et al. |
| 2001/0005785 A1 | 6/2001 | Sachse |
| 2001/0007070 A1 | 7/2001 | Stewart et al. |
| 2001/0020174 A1 | 9/2001 | Koblish |
| 2001/0031971 A1 | 10/2001 | Dretler et al. |
| 2002/0004631 A1 | 1/2002 | Jenkins et al. |
| 2002/0004644 A1 | 1/2002 | Koblish |
| 2002/0022864 A1 | 2/2002 | Mahvi et al. |
| 2002/0062123 A1 | 5/2002 | McClurken et al. |
| 2002/0062124 A1 | 5/2002 | Keane |
| 2002/0087208 A1 | 7/2002 | Koblish et al. |
| 2002/0139379 A1 | 10/2002 | Edwards et al. |
| 2002/0165532 A1 | 11/2002 | Hill et al. |
| 2002/0169444 A1 | 11/2002 | Mest et al. |
| 2002/0177765 A1 | 11/2002 | Bowe et al. |
| 2002/0183682 A1 | 12/2002 | Darvish et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0060857 A1 | 3/2003 | Perrson et al. |
| 2003/0060858 A1 | 3/2003 | Kieval et al. |
| 2003/0065317 A1 | 4/2003 | Rudie et al. |
| 2003/0074039 A1 | 4/2003 | Puskas |
| 2003/0088244 A1 | 5/2003 | Swanson et al. |
| 2003/0092995 A1 | 5/2003 | Thompson |
| 2003/0097119 A1* | 5/2003 | Garabedian ......... A61M 25/005 604/524 |
| 2003/0125790 A1 | 7/2003 | Fastovsky et al. |
| 2003/0139689 A1 | 7/2003 | Shturman et al. |
| 2003/0153967 A1 | 8/2003 | Koblish et al. |
| 2003/0158584 A1 | 8/2003 | Cates et al. |
| 2003/0181897 A1 | 9/2003 | Thomas et al. |
| 2003/0199863 A1 | 10/2003 | Swanson et al. |
| 2003/0204187 A1 | 10/2003 | Hintringer et al. |
| 2003/0216792 A1 | 11/2003 | Levin et al. |
| 2003/0220639 A1 | 11/2003 | Chapelon et al. |
| 2003/0229340 A1 | 12/2003 | Sherry et al. |
| 2003/0233099 A1 | 12/2003 | Danaek et al. |
| 2004/0006359 A1 | 1/2004 | Laguna |
| 2004/0010289 A1 | 1/2004 | Biggs et al. |
| 2004/0024371 A1 | 2/2004 | Plicchi et al. |
| 2004/0030375 A1 | 2/2004 | Pierce |
| 2004/0049181 A1 | 3/2004 | Stewart et al. |
| 2004/0073206 A1 | 4/2004 | Foley et al. |
| 2004/0082978 A1 | 4/2004 | Harrison et al. |
| 2004/0088002 A1 | 5/2004 | Boyle et al. |
| 2004/0122421 A1 | 6/2004 | Wood |
| 2004/0167509 A1 | 8/2004 | Taimisto |
| 2004/0215186 A1 | 10/2004 | Cornelius et al. |
| 2005/0004515 A1 | 1/2005 | Hart et al. |
| 2005/0010095 A1 | 1/2005 | Stewart et al. |
| 2005/0015084 A1* | 1/2005 | Hill, III ............. A61B 18/1492 606/41 |
| 2005/0033137 A1 | 2/2005 | Oral et al. |
| 2005/0070887 A1 | 3/2005 | Taimisto et al. |
| 2005/0080409 A1 | 4/2005 | Young et al. |
| 2005/0096647 A1 | 5/2005 | Steinke et al. |

(56) References Cited

U.S. PATENT DOCUMENTS

| | | |
|---|---|---|
| 2005/0187579 A1 | 8/2005 | Danek et al. |
| 2005/0228286 A1 | 10/2005 | Messerly et al. |
| 2005/0228460 A1 | 10/2005 | Levin et al. |
| 2005/0273006 A1 | 12/2005 | Stewart et al. |
| 2006/0004323 A1 | 1/2006 | Chang et al. |
| 2006/0004346 A1 | 1/2006 | Begg |
| 2006/0025762 A1 | 2/2006 | Mohan et al. |
| 2006/0025765 A1 | 2/2006 | Landman et al. |
| 2006/0074403 A1 | 4/2006 | Rafiee |
| 2006/0085054 A1 | 4/2006 | Zikorus et al. |
| 2006/0089637 A1* | 4/2006 | Werneth ............ A61B 18/1492 606/41 |
| 2006/0095029 A1 | 5/2006 | Young et al. |
| 2006/0100618 A1 | 5/2006 | Chan et al. |
| 2006/0122587 A1 | 6/2006 | Sharareh |
| 2006/0135870 A1 | 6/2006 | Webler |
| 2006/0135953 A1 | 6/2006 | Kania et al. |
| 2006/0142753 A1 | 6/2006 | Francischelli et al. |
| 2006/0167498 A1 | 7/2006 | DiLorenzo |
| 2006/0184221 A1 | 8/2006 | Stewart et al. |
| 2006/0206150 A1 | 9/2006 | Demarais et al. |
| 2006/0224153 A1 | 10/2006 | Fischell et al. |
| 2006/0241366 A1 | 10/2006 | Falwell et al. |
| 2006/0247618 A1 | 11/2006 | Kaplan et al. |
| 2006/0247619 A1 | 11/2006 | Kaplan et al. |
| 2006/0263393 A1 | 11/2006 | Demopulos et al. |
| 2006/0271111 A1 | 11/2006 | Demarais et al. |
| 2006/0276846 A1 | 12/2006 | Malecki et al. |
| 2006/0287644 A1 | 12/2006 | Inganas et al. |
| 2007/0027390 A1 | 2/2007 | Maschke et al. |
| 2007/0043409 A1 | 2/2007 | Brian et al. |
| 2007/0049924 A1 | 3/2007 | Rahn |
| 2007/0067008 A1 | 3/2007 | Scheiner et al. |
| 2007/0073151 A1 | 3/2007 | Lee |
| 2007/0083194 A1 | 4/2007 | Kunis et al. |
| 2007/0100405 A1 | 5/2007 | Thompson et al. |
| 2007/0106247 A1 | 5/2007 | Burnett et al. |
| 2007/0106293 A1 | 5/2007 | Oral et al. |
| 2007/0112327 A1 | 5/2007 | Yun et al. |
| 2007/0129720 A1 | 6/2007 | Demarais et al. |
| 2007/0149963 A1 | 6/2007 | Matsukuma et al. |
| 2007/0156114 A1 | 7/2007 | Worley et al. |
| 2007/0179496 A1 | 8/2007 | Swoyer et al. |
| 2007/0197891 A1 | 8/2007 | Shachar et al. |
| 2007/0225781 A1 | 9/2007 | Saadat et al. |
| 2007/0265687 A1 | 11/2007 | Deem et al. |
| 2007/0270779 A1 | 11/2007 | Jacobs et al. |
| 2007/0299438 A1 | 12/2007 | Holzbaur et al. |
| 2008/0004658 A1 | 1/2008 | Malecki et al. |
| 2008/0015562 A1 | 1/2008 | Hong et al. |
| 2008/0021408 A1 | 1/2008 | Jacobsen et al. |
| 2008/0045921 A1 | 2/2008 | Anderson et al. |
| 2008/0064957 A1 | 3/2008 | Spence |
| 2008/0071269 A1 | 3/2008 | Hilario et al. |
| 2008/0077119 A1 | 3/2008 | Snyder et al. |
| 2008/0086047 A1 | 4/2008 | McDaniel et al. |
| 2008/0091193 A1 | 4/2008 | Kauphusman et al. |
| 2008/0097398 A1 | 4/2008 | Mitelberg et al. |
| 2008/0108867 A1 | 5/2008 | Zhou |
| 2008/0108975 A1 | 5/2008 | Appling et al. |
| 2008/0109011 A1 | 5/2008 | Thenuwara et al. |
| 2008/0140072 A1 | 6/2008 | Stangenes et al. |
| 2008/0172104 A1 | 7/2008 | Kieval et al. |
| 2008/0177205 A1 | 7/2008 | Rama et al. |
| 2008/0183187 A1 | 7/2008 | Bly |
| 2008/0255539 A1 | 10/2008 | Booth |
| 2008/0287918 A1 | 11/2008 | Rosenman et al. |
| 2008/0288039 A1 | 11/2008 | Reddy |
| 2008/0300587 A1 | 11/2008 | Anderson |
| 2008/0319513 A1 | 12/2008 | Pu et al. |
| 2009/0012465 A1 | 1/2009 | Latini |
| 2009/0018534 A1 | 1/2009 | Taimisto et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0069671 A1 | 3/2009 | Anderson |
| 2009/0118620 A1 | 5/2009 | Tgavalekos et al. |
| 2009/0149848 A1* | 6/2009 | Werneth ............ A61B 18/1492 606/33 |
| 2009/0157048 A1 | 6/2009 | Sutermeister et al. |
| 2009/0163850 A1 | 6/2009 | Betts et al. |
| 2009/0171333 A1 | 7/2009 | Hon |
| 2009/0221955 A1 | 9/2009 | Babaev |
| 2009/0287202 A1 | 11/2009 | Ingle et al. |
| 2009/0306650 A1 | 12/2009 | Govari et al. |
| 2009/0306651 A1* | 12/2009 | Schneider ............ A61B 5/0422 606/41 |
| 2009/0312606 A1 | 12/2009 | Dayton et al. |
| 2010/0030061 A1 | 2/2010 | Canfield et al. |
| 2010/0030112 A1 | 2/2010 | Anderson et al. |
| 2010/0069882 A1 | 3/2010 | Jennings et al. |
| 2010/0137860 A1 | 6/2010 | Demarais et al. |
| 2010/0137952 A1 | 6/2010 | Demarais et al. |
| 2010/0168740 A1 | 7/2010 | Stewart et al. |
| 2010/0168777 A1 | 7/2010 | Stangenes et al. |
| 2010/0174282 A1 | 7/2010 | Demarais et al. |
| 2010/0179512 A1 | 7/2010 | Chong et al. |
| 2010/0191112 A1 | 7/2010 | Demarais et al. |
| 2010/0204692 A1 | 8/2010 | Stewart et al. |
| 2010/0217184 A1 | 8/2010 | Koblish et al. |
| 2010/0222851 A1 | 9/2010 | Deem et al. |
| 2010/0222854 A1 | 9/2010 | Demarais et al. |
| 2010/0249604 A1 | 9/2010 | Hastings et al. |
| 2010/0261990 A1 | 10/2010 | Gillis et al. |
| 2010/0312141 A1 | 12/2010 | Keast et al. |
| 2010/0324482 A1 | 12/2010 | Farnholtz |
| 2011/0021976 A1 | 1/2011 | Li et al. |
| 2011/0028962 A1 | 2/2011 | Werneth et al. |
| 2011/0034989 A1 | 2/2011 | Al-Marashi et al. |
| 2011/0054464 A1 | 3/2011 | Werneth et al. |
| 2011/0054465 A1 | 3/2011 | Werneth et al. |
| 2011/0071400 A1 | 3/2011 | Hastings et al. |
| 2011/0071401 A1 | 3/2011 | Hastings et al. |
| 2011/0112476 A1 | 5/2011 | Kauphusman et al. |
| 2011/0144639 A1 | 6/2011 | Govari |
| 2011/0160719 A1 | 6/2011 | Govari et al. |
| 2011/0264086 A1 | 10/2011 | Ingle |
| 2011/0270173 A1 | 11/2011 | Gibson et al. |
| 2011/0306851 A1 | 12/2011 | Wang |
| 2011/0319908 A1 | 12/2011 | Thenuwara et al. |
| 2012/0010607 A1 | 1/2012 | Malecki et al. |
| 2012/0029509 A1 | 2/2012 | Smith |
| 2012/0029510 A1 | 2/2012 | Haverkost |
| 2012/0029513 A1 | 2/2012 | Smith et al. |
| 2012/0035615 A1 | 2/2012 | Koester et al. |
| 2012/0059241 A1 | 3/2012 | Hastings et al. |
| 2012/0078076 A1 | 3/2012 | Stewart et al. |
| 2012/0101413 A1 | 4/2012 | Beetel et al. |
| 2012/0101553 A1 | 4/2012 | Reddy |
| 2012/0101561 A1* | 4/2012 | Porter ............ A61F 2/95 623/1.11 |
| 2012/0116382 A1 | 5/2012 | Ku et al. |
| 2012/0116383 A1* | 5/2012 | Mauch ............ A61B 18/1492 606/33 |
| 2012/0116438 A1 | 5/2012 | Salahieh et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130368 A1 | 5/2012 | Jenson |
| 2012/0143293 A1 | 6/2012 | Mauch et al. |
| 2012/0172714 A1 | 7/2012 | Govari et al. |
| 2012/0172837 A1 | 7/2012 | Demarais et al. |
| 2012/0191083 A1 | 7/2012 | Moll et al. |
| 2012/0197246 A1 | 8/2012 | Mauch |
| 2012/0265066 A1 | 10/2012 | Crow et al. |
| 2012/0277842 A1 | 11/2012 | Kunis |
| 2012/0290053 A1 | 11/2012 | Zhang et al. |
| 2012/0310065 A1 | 12/2012 | Falwell et al. |
| 2012/0310239 A1 | 12/2012 | Stewart et al. |
| 2012/0323233 A1 | 12/2012 | Maguire et al. |
| 2012/0330121 A1 | 12/2012 | Anderson et al. |
| 2013/0035681 A1 | 2/2013 | Subramaniam et al. |
| 2013/0053876 A1 | 2/2013 | Ogle |
| 2013/0066316 A1 | 3/2013 | Steinke et al. |

(56) References Cited

U.S. PATENT DOCUMENTS

| | | |
|---|---|---|
| 2013/0085360 A1 | 4/2013 | Grunewald |
| 2013/0090637 A1 | 4/2013 | Sliwa |
| 2013/0090647 A1 | 4/2013 | Smith |
| 2013/0090649 A1 | 4/2013 | Smith et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0109987 A1 | 5/2013 | Kunis et al. |
| 2013/0123770 A1 | 5/2013 | Smith |
| 2013/0131667 A1 | 5/2013 | Jenson et al. |
| 2013/0165920 A1 | 6/2013 | Weber et al. |
| 2013/0165921 A1 | 6/2013 | Sutermeister et al. |
| 2013/0172872 A1 | 7/2013 | Subramaniam et al. |
| 2013/0172879 A1 | 7/2013 | Sutermeister et al. |
| 2013/0172881 A1 | 7/2013 | Hill et al. |
| 2013/0184642 A1 | 7/2013 | O'Donnell et al. |
| 2013/0184703 A1 | 7/2013 | Shireman et al. |
| 2013/0184773 A1 | 7/2013 | Libbus et al. |
| 2013/0211399 A1* | 8/2013 | Caples ............ A61B 18/1492 606/41 |
| 2013/0253628 A1 | 9/2013 | Smith et al. |
| 2013/0274614 A1 | 10/2013 | Shimada et al. |
| 2013/0274730 A1 | 10/2013 | Anderson et al. |
| 2013/0274731 A1 | 10/2013 | Anderson et al. |
| 2013/0274737 A1 | 10/2013 | Wang et al. |
| 2013/0282000 A1 | 10/2013 | Parsonage |
| 2013/0282084 A1 | 10/2013 | Mathur et al. |
| 2013/0289686 A1 | 10/2013 | Masson et al. |
| 2013/0304047 A1 | 11/2013 | Grunewald et al. |
| 2013/0304052 A1 | 11/2013 | Rizq et al. |
| 2013/0304062 A1 | 11/2013 | Chan et al. |
| 2014/0058376 A1 | 2/2014 | Horn et al. |
| 2014/0094787 A1 | 4/2014 | Reynolds |
| 2014/0121641 A1 | 5/2014 | Fischell et al. |
| 2014/0121644 A1 | 5/2014 | Fischell et al. |
| 2014/0135755 A1 | 5/2014 | Sutermeister et al. |
| 2014/0180277 A1* | 6/2014 | Chen ............... A61B 18/1492 606/41 |
| 2014/0213873 A1 | 7/2014 | Wang |
| 2014/0214018 A1 | 7/2014 | Behar et al. |
| 2014/0214026 A1 | 7/2014 | Degen |
| 2014/0221805 A1 | 8/2014 | Wang |
| 2014/0243821 A1 | 8/2014 | Salahieh et al. |
| 2014/0249524 A1 | 9/2014 | Kocur |
| 2014/0257280 A1 | 9/2014 | Hanson et al. |
| 2014/0257281 A1 | 9/2014 | Squire et al. |
| 2014/0276613 A1 | 9/2014 | Goodman et al. |
| 2014/0276747 A1 | 9/2014 | Abunassar et al. |
| 2014/0276752 A1 | 9/2014 | Wang et al. |
| 2014/0276787 A1 | 9/2014 | Wang et al. |
| 2014/0276789 A1 | 9/2014 | Dandler et al. |
| 2014/0303617 A1 | 10/2014 | Shimada |
| 2014/0350553 A1 | 11/2014 | Okuyama |
| 2014/0358079 A1 | 12/2014 | Fischell et al. |
| 2014/0378967 A1 | 12/2014 | Willard et al. |
| 2015/0025525 A1 | 1/2015 | Willard et al. |
| 2015/0057655 A1 | 2/2015 | Osypka |
| 2015/0066013 A1 | 3/2015 | Salahieh et al. |
| 2015/0105659 A1 | 4/2015 | Salahieh et al. |
| 2015/0112329 A1 | 4/2015 | Ng |
| 2015/0126992 A1 | 5/2015 | Mogul |
| 2015/0223866 A1 | 8/2015 | Buelna et al. |
| 2015/0223877 A1 | 8/2015 | Behar et al. |
| 2015/0265339 A1 | 9/2015 | Lindquist et al. |
| 2015/0289770 A1 | 10/2015 | Wang |
| 2016/0175040 A1 | 6/2016 | Magana et al. |
| 2016/0175044 A1 | 6/2016 | Abunassar et al. |
| 2016/0175582 A1 | 6/2016 | Serna et al. |
| 2016/0374568 A1 | 12/2016 | Wang |
| 2017/0042610 A1 | 2/2017 | Smith et al. |

FOREIGN PATENT DOCUMENTS

| | | |
|---|---|---|
| CN | 102125460 | 7/2011 |
| CN | 102125725 | 7/2011 |
| CN | 102198015 | 9/2011 |
| CN | 102274075 | 12/2011 |
| CN | 102488552 | 6/2012 |
| CN | 202386778 | 8/2012 |
| CN | 202426649 | 9/2012 |
| CN | 102772249 A | 11/2012 |
| CN | 202537649 | 11/2012 |
| CN | 202538132 | 11/2012 |
| CN | 102885648 | 1/2013 |
| CN | 102908188 | 2/2013 |
| CN | 202761434 | 3/2013 |
| CN | 202843784 | 4/2013 |
| CN | 105167840 A | 12/2015 |
| CN | 105326562 A | 2/2016 |
| CN | 205433878 U | 8/2016 |
| CN | 205433879 U | 8/2016 |
| DE | 29909082 | 7/1999 |
| DE | 10252325 | 5/2004 |
| DE | 10257146 | 6/2004 |
| DE | 102005041601 | 4/2007 |
| DE | 102012104705 | 12/2013 |
| EP | 0132344 | 1/1985 |
| EP | 0348136 | 12/1989 |
| EP | 0352955 | 1/1990 |
| EP | 510624 | 10/1992 |
| EP | 0512359 | 11/1992 |
| EP | 0542246 | 5/1993 |
| EP | 626818 | 12/1994 |
| EP | 647435 | 4/1995 |
| EP | 652026 | 5/1995 |
| EP | 664990 | 8/1995 |
| EP | 0680351 | 11/1995 |
| EP | 727184 | 8/1996 |
| EP | 728495 | 8/1996 |
| EP | 0732080 | 9/1996 |
| EP | 757575 | 2/1997 |
| EP | 778043 | 6/1997 |
| EP | 779079 | 6/1997 |
| EP | 0787019 | 8/1997 |
| EP | 0821602 | 2/1998 |
| EP | 0834289 | 4/1998 |
| EP | 862478 | 9/1998 |
| EP | 865256 | 9/1998 |
| EP | 868160 A1 | 10/1998 |
| EP | 0868923 | 10/1998 |
| EP | 873760 | 10/1998 |
| EP | 0916360 | 5/1999 |
| EP | 0937481 | 8/1999 |
| EP | 944353 | 9/1999 |
| EP | 0951244 | 10/1999 |
| EP | 963191 | 12/1999 |
| EP | 0984806 | 3/2000 |
| EP | 1042990 | 10/2000 |
| EP | 1233716 | 8/2002 |
| EP | 1286625 | 3/2003 |
| EP | 1297795 A1 | 4/2003 |
| EP | 1326550 | 7/2003 |
| EP | 1332724 A1 | 8/2003 |
| EP | 1374943 | 1/2004 |
| EP | 1383567 A1 | 1/2004 |
| EP | 1656963 | 5/2006 |
| EP | 1709922 | 10/2006 |
| EP | 1733689 | 12/2006 |
| EP | 1768732 | 4/2007 |
| EP | 1787674 | 5/2007 |
| EP | 1802370 | 7/2007 |
| EP | 1824548 | 8/2007 |
| EP | 1827558 | 9/2007 |
| EP | 1857134 | 11/2007 |
| EP | 1906853 | 4/2008 |
| EP | 1968679 | 9/2008 |
| EP | 2027882 | 2/2009 |
| EP | 1009303 | 6/2009 |
| EP | 2208474 | 7/2010 |
| EP | 2263588 | 12/2010 |

(56) References Cited

FOREIGN PATENT DOCUMENTS

| | | |
|---|---|---|
| EP | 2320821 | 5/2011 |
| EP | 2329859 A1 | 6/2011 |
| EP | 2340765 | 7/2011 |
| EP | 2389974 | 11/2011 |
| EP | 2398540 | 12/2011 |
| EP | 2445568 | 5/2012 |
| EP | 2519173 | 11/2012 |
| EP | 2558016 | 2/2013 |
| EP | 2570154 A2 | 3/2013 |
| EP | 2598069 | 6/2013 |
| EP | 2645955 A1 | 10/2013 |
| EP | 2664295 | 11/2013 |
| EP | 2694158 | 2/2014 |
| EP | 2709517 A1 | 3/2014 |
| EP | 2747688 | 7/2014 |
| EP | 2759275 | 7/2014 |
| EP | 2759314 | 7/2014 |
| EP | 2760532 | 8/2014 |
| EP | 2804554 | 11/2014 |
| EP | 2836151 A2 | 2/2015 |
| EP | 2839802 A1 | 2/2015 |
| EP | 2890321 A1 | 7/2015 |
| EP | 2900160 | 8/2015 |
| EP | 2900161 | 8/2015 |
| EP | 2907464 A1 | 8/2015 |
| EP | 2990070 | 3/2016 |
| EP | 3003191 A1 | 4/2016 |
| EP | 3010436 | 4/2016 |
| EP | 3049007 A1 | 8/2016 |
| EP | 2768563 | 11/2016 |
| EP | 3102132 A1 | 12/2016 |
| EP | 3123973 A1 | 2/2017 |
| EP | 3148467 | 4/2017 |
| JP | 355137141 | 9/1996 |
| JP | 2003116904 | 4/2003 |
| JP | 2015119831 A | 7/2015 |
| JP | 2016086999 A | 5/2016 |
| WO | WO-9000036 | 1/1990 |
| WO | WO-9101772 | 2/1991 |
| WO | WO-9115254 | 10/1991 |
| WO | WO-9215356 | 9/1992 |
| WO | WO-9220291 | 11/1992 |
| WO | 1994007446 | 4/1994 |
| WO | WO-9419039 | 9/1994 |
| WO | WO-9421168 | 9/1994 |
| WO | 1994028809 | 12/1994 |
| WO | WO-9513111 | 5/1995 |
| WO | WO-9520416 | 8/1995 |
| WO | WO-1995025472 | 9/1995 |
| WO | 1995031142 | 11/1995 |
| WO | WO-9600036 | 1/1996 |
| WO | WO-9632980 | 10/1996 |
| WO | WO-9638196 | 12/1996 |
| WO | WO-9717892 | 5/1997 |
| WO | WO-9729800 | 8/1997 |
| WO | WO-1997036548 | 10/1997 |
| WO | WO-9748435 | 12/1997 |
| WO | WO-9802201 | 1/1998 |
| WO | WO-1998018393 A1 | 5/1998 |
| WO | WO-9833469 | 8/1998 |
| WO | 1998042403 | 10/1998 |
| WO | WO-9843530 | 10/1998 |
| WO | WO-9848885 | 11/1998 |
| WO | WO-9850098 | 11/1998 |
| WO | WO-9852637 | 11/1998 |
| WO | WO-9900060 | 1/1999 |
| WO | WO-9911313 | 3/1999 |
| WO | WO-9923958 | 5/1999 |
| WO | WO-9952421 | 10/1999 |
| WO | WO-9956801 | 11/1999 |
| WO | WO-9962413 | 12/1999 |
| WO | WO-00001313 | 1/2000 |
| WO | WO-00056237 | 9/2000 |
| WO | WO-00067832 | 11/2000 |
| WO | WO-0122897 | 4/2001 |
| WO | WO-2001022897 | 4/2001 |
| WO | 2001037723 | 5/2001 |
| WO | 2001037746 | 5/2001 |
| WO | WO-0137723 | 5/2001 |
| WO | WO-0137746 | 5/2001 |
| WO | WO-2001037746 | 5/2001 |
| WO | WO-2001070114 | 9/2001 |
| WO | WO-2001074255 | 10/2001 |
| WO | WO-0180758 | 11/2001 |
| WO | WO-0230310 | 4/2002 |
| WO | WO-0245608 | 6/2002 |
| WO | 2002080766 | 10/2002 |
| WO | WO-02083017 | 10/2002 |
| WO | WO-02087453 | 11/2002 |
| WO | WO-02089687 | 11/2002 |
| WO | WO-02089908 | 11/2002 |
| WO | 2003022167 | 3/2003 |
| WO | WO-2003077781 | 9/2003 |
| WO | WO-03082080 | 10/2003 |
| WO | WO-2004100813 | 11/2004 |
| WO | WO-2005030072 | 4/2005 |
| WO | WO-2005041748 | 5/2005 |
| WO | WO-2005051216 | 6/2005 |
| WO | WO-2005070491 | 8/2005 |
| WO | WO-2005110528 | 11/2005 |
| WO | WO-2006/009588 | 1/2006 |
| WO | WO-2006020920 | 2/2006 |
| WO | WO-2006041881 | 4/2006 |
| WO | WO-2006065949 | 6/2006 |
| WO | WO-2006092000 | 9/2006 |
| WO | 2006105121 | 10/2006 |
| WO | WO-2007001981 | 1/2007 |
| WO | WO-2007008954 | 1/2007 |
| WO | WO-2007059277 | 5/2007 |
| WO | 2007078997 | 7/2007 |
| WO | WO-2007117359 | 10/2007 |
| WO | WO-2007128064 | 11/2007 |
| WO | 2008010150 | 1/2008 |
| WO | 2008036281 | 3/2008 |
| WO | 2008049084 | 4/2008 |
| WO | WO-2008064399 | 6/2008 |
| WO | WO-2008101244 | 8/2008 |
| WO | WO-2008139347 | 11/2008 |
| WO | 2009082635 | 7/2009 |
| WO | 2009088678 | 7/2009 |
| WO | WO-2009082635 A1 | 7/2009 |
| WO | WO-2009121017 | 10/2009 |
| WO | 2009137819 | 11/2009 |
| WO | WO-2010048676 | 5/2010 |
| WO | WO-2010091701 | 8/2010 |
| WO | WO-2010120835 | 10/2010 |
| WO | 2010134503 | 11/2010 |
| WO | WO-2011015218 | 2/2011 |
| WO | WO-2011019838 | 2/2011 |
| WO | WO-2011/060200 | 5/2011 |
| WO | WO-2011055143 A2 | 5/2011 |
| WO | WO-2011056311 | 5/2011 |
| WO | WO-2011082279 | 7/2011 |
| WO | WO-2011130534 | 10/2011 |
| WO | WO-2012075156 | 6/2012 |
| WO | WO-2012100095 | 7/2012 |
| WO | WO-2012130337 | 10/2012 |
| WO | WO-2012131107 | 10/2012 |
| WO | WO-2012154219 | 11/2012 |
| WO | WO-2012154796 | 11/2012 |
| WO | WO-2013016203 | 1/2013 |
| WO | WO-2013028993 | 2/2013 |
| WO | WO-2013030807 | 3/2013 |
| WO | WO-2013040201 | 3/2013 |
| WO | WO-2013/055685 | 4/2013 |
| WO | WO-2013049601 | 4/2013 |
| WO | WO-2013055537 | 4/2013 |
| WO | WO-2013055815 | 4/2013 |
| WO | WO-2013055826 | 4/2013 |
| WO | WO-2013056672 | 4/2013 |
| WO | WO-2013058962 | 4/2013 |
| WO | WO-2013101452 | 7/2013 |
| WO | WO-2013106054 | 7/2013 |
| WO | WO-2013109318 | 7/2013 |

(56) References Cited

FOREIGN PATENT DOCUMENTS

| WO | WO-2013154776 | 10/2013 |
|---|---|---|
| WO | WO-2013158676 | 10/2013 |
| WO | WO-2013158678 | 10/2013 |
| WO | WO-2013165920 | 11/2013 |
| WO | WO-2014012282 | 1/2014 |
| WO | WO-2014036160 | 3/2014 |
| WO | WO-2014036163 | 3/2014 |
| WO | WO-2014056460 | 4/2014 |
| WO | 2014174662 | 10/2014 |
| WO | WO-2014163987 | 10/2014 |
| WO | WO-2014163990 | 10/2014 |
| WO | WO-2014176785 A1 | 11/2014 |
| WO | 2015161790 | 10/2015 |
| WO | 2016090175 | 6/2016 |
| WO | WO-2016094938 A1 | 6/2016 |

OTHER PUBLICATIONS

International Search Report, PCT/US01/044977, dated Jun. 7, 2002, 6 Pages.
International Search Report, PCT/US02/07661, dated Aug. 13, 2002, 5 Pages.
International Search Report, PCT/US03/031339, dated Feb. 18, 2004, 3 Pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter, "Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.

(56) References Cited

OTHER PUBLICATIONS

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europer-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards[TM]" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." Eurolntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; dated Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." Am. J. Roentgenol,174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." Clin. Sci, 87: 13-19 (1994).

(56) References Cited

OTHER PUBLICATIONS

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:ll-17-ll-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot$^{TM}$ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

Renal Denervation (RDN), Symplicity RDN System Common Q&A (2011), 4 pages, http://www.medtronic.com/rdn/mediakit/RDN%20FAQ.pdf.

Schauerte, P., et al. "Catheter ablation of cardiac autonomic nerves for prevention of vagal atrial fibrillation." Circulation, 102:2774-2780 (2000).

Schlaich, Markus et al., "Renal Denervation in Human Hypertension: Mechanisms, Current Findings, and Future Prospects." Curr Hypertens Rep, vol. 14, 2012, 7 pages.

Schmid, Axel et al., "Does Renal Artery Supply Indicate Treatment Success of Renal Denervation." Cardiovasc Intervent Radiol, vol. 36, 2013, 5 pages.

Schmieder, Roland E. et al., "Updated ESH position paper on interventional therapy of resistant hypertension." EuroIntervention, vol. 9, 2013, 9 pages.

Sievert, Horst, "Novelty Award EuroPCR 2010." Euro PCR, 2010, 15 pages.

Solis-Herruzo et al., "Effects of lumbar sympathetic block on kidney function in cirrhotic patients with hepatorenal syndrome," J. Hepatol. 5 (1987), pp. 167-173.

Stella, A., et al., "Effects of reversible renal denervation on haemodynamic and excretory functions on the ipsilateral and contralateral kidney in the cat." Hypertension, 4:181-188 (1986).

Stouffer, G. A. et al., "Catheter-based renal denervation in the treatment of resistant hypertension." Journal of Molecular and Cellular Cardiology, vol. 62, 2013, 6 pages.

Swartz, J.F., et al., "Radiofrequency endocardial catheter ablation of accessory atrioventricular pathway atrial insertion sites." Circulation, 87: 487-499 (1993).

Uchida, F., et al., "Effect of radiofrequency catheter ablation on parasympathetic denervation: A comparison of three different ablation sites." PACE, 21:2517-2521 (1998).

Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.

Weinstock, M., et al., "Renal denervation prevents sodium retention and hypertension in salt sensitive rabbits with genetic baroreflex impairment." Clinical Science, 90:287-293 (1996).

Wilcox, Josiah N., Scientific Basis Behind Renal Denervation for the Control of Hypertension, ICI 2012, Dec. 5-6, 2012. 38 pages.

Worthley, Stephen et al., "Safety and efficacy of a multi-electrode renal sympathetic denervation system in resistant hypertension: the EnligHTN I trial." European Heart Journal, vol. 34, 2013, 9 pages.

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Miller, Reed, "Finding A Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

European Search Report for European Application No. 13159256, dated Oct. 17, 2013, 6 pages.

(56) References Cited

OTHER PUBLICATIONS

Claudine Jaboro, "An in vivo study of the biocompatibility of classic and novel device materials on the central nervous system", (Jan. 1, 2007), ETD Collection for Wayne State University. Paper AAI3310737, 2 pages. <http://digitalcommons.wayne.edu/dissertations/AAI3310737>.

European Search Report dated Feb. 22, 2013; Application No. 12180432.2; Applicant: Medtronic Ardian Luxembourg S.a.r.l.; 6 pages.

European Search Report dated Feb. 28, 2013; European Application No. 12180427.2; Applicant: Medtronic Ardian Luxembourg S.a.r.l.; 4 pages.

European Search Report dated Jan. 30, 2013; Application No. 12180428.0; Applicant: Medtronic Ardian Luxembourg S.a.r.l.; 6 pages.

European Search Report dated Jan. 30, 2013; Application No. 12180430.6; Applicant: Medtronic Ardian Luxembourg S.a.r.l.; 6 pages.

European Search Report dated Jan. 30, 2013; Application No. 12180431.4; Applicant: Medtronic Ardian Luxembourg S.a.r.l.; 6 pages.

European Search Report dated Jan. 30, 2013; European Application No. 12180426.4; Applicant: Medtronic Ardian Luxembourg S.a.r.l.; 6 pages.

Hanker et al., "Biomedical Materials and Devices," Materials Research Society Symposium Proceedings, vol. 110, Dec. 4, 1987, Boston Massachusetts, USA, 8 pages.

International Search Report and Written Opinion dated Feb. 16, 2012, International Application No. PCT/US2011/057754, 13 pages.
International Search Report and Written Opinion dated Jan. 20, 2012, International Application No. PCT/US2011/057756, 10 pages.
International Search Report and Written Opinion dated Jan. 23, 2012, International Application No. PCT/US2011/057761, 13 pages.
Lahiri D. et al. Boron nitride nanotube reinforced polylactide-polycaprolactone copolymer composite: Mechanical properties and cytocompatibility with osteoblasts and macrophages in vitro. Acta Biomater (2010), doi: 10.1016/j.actbio.2010.02.44.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Opposition to European Patent No. 2465470, Granted Oct. 28, 2015, Date of Opposition Jul. 27, 2016, 34 pp.
Pieper, et al., "Design and Implementation of a New Computerized System for Intraoperative Cardiac Mapping" Journal of Applied Physiology, 1991, vol. 71 (4), pp. 1529-1539.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.

* cited by examiner

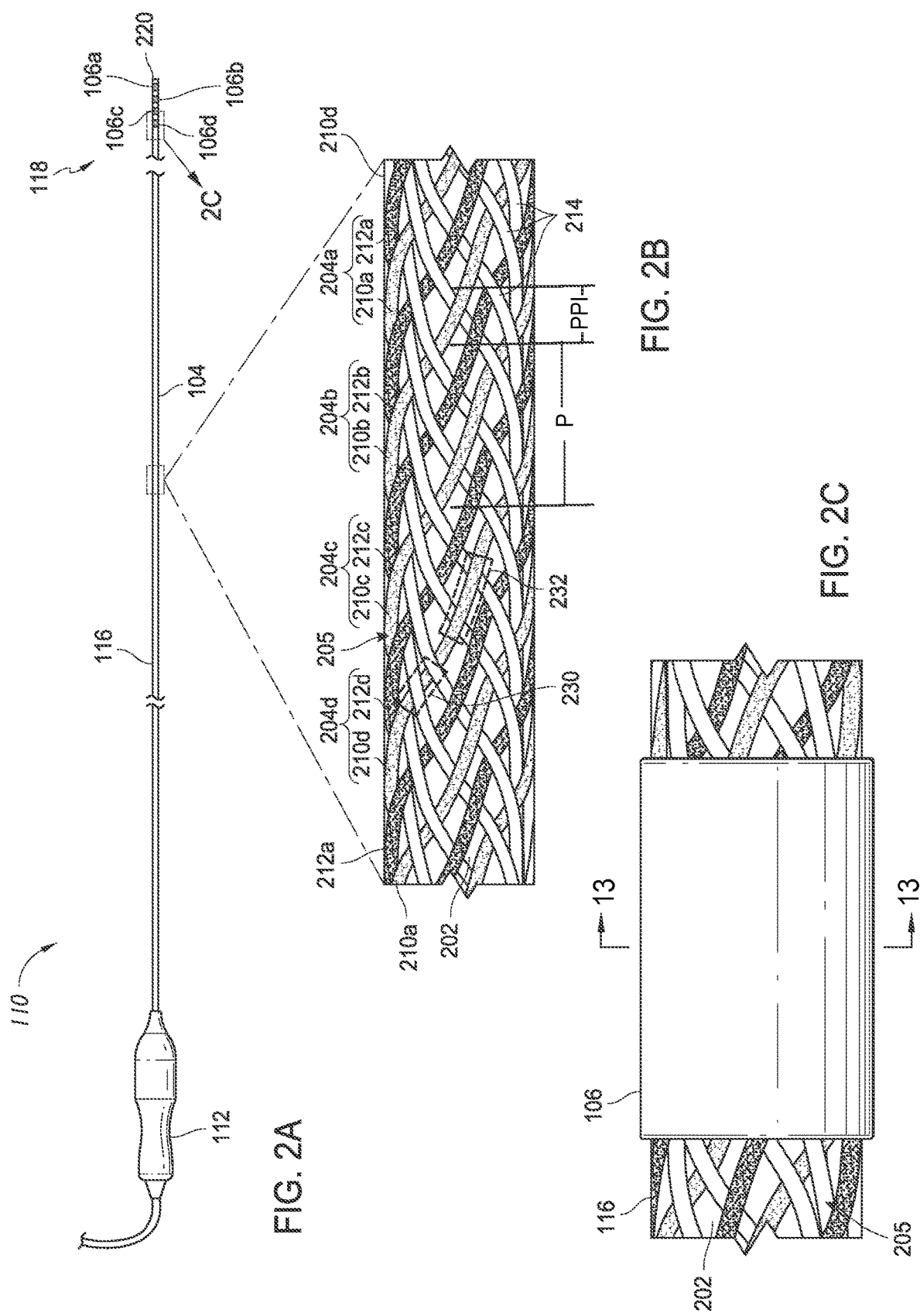

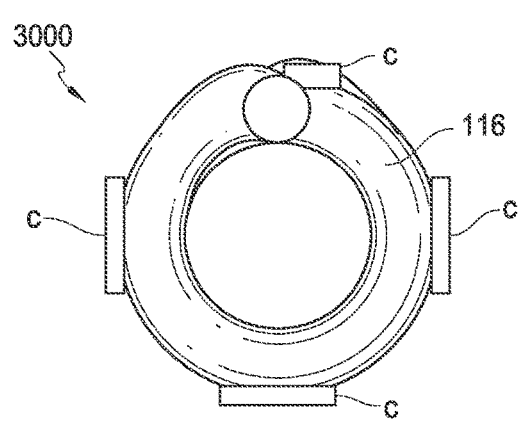
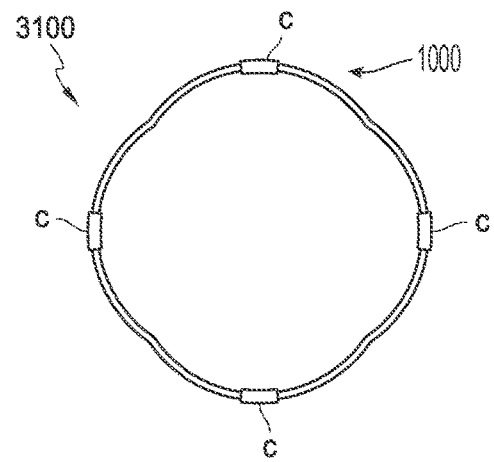
FIG. 9  FIG. 10
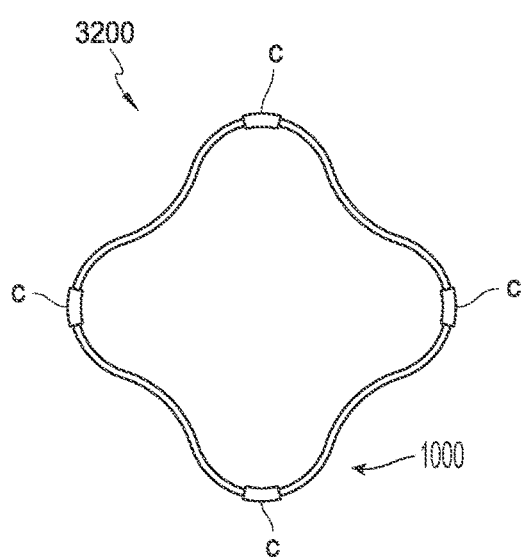
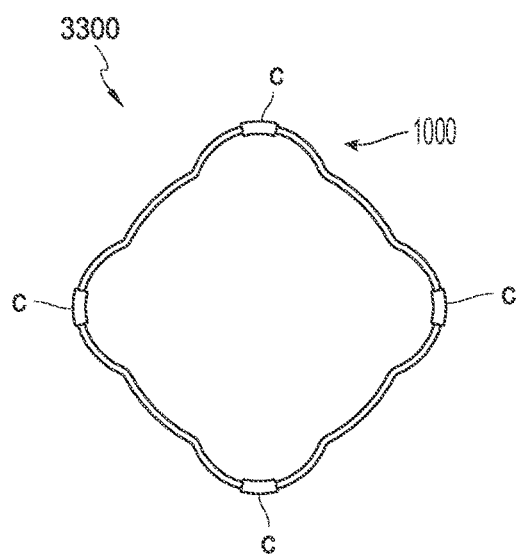
FIG. 11  FIG. 12

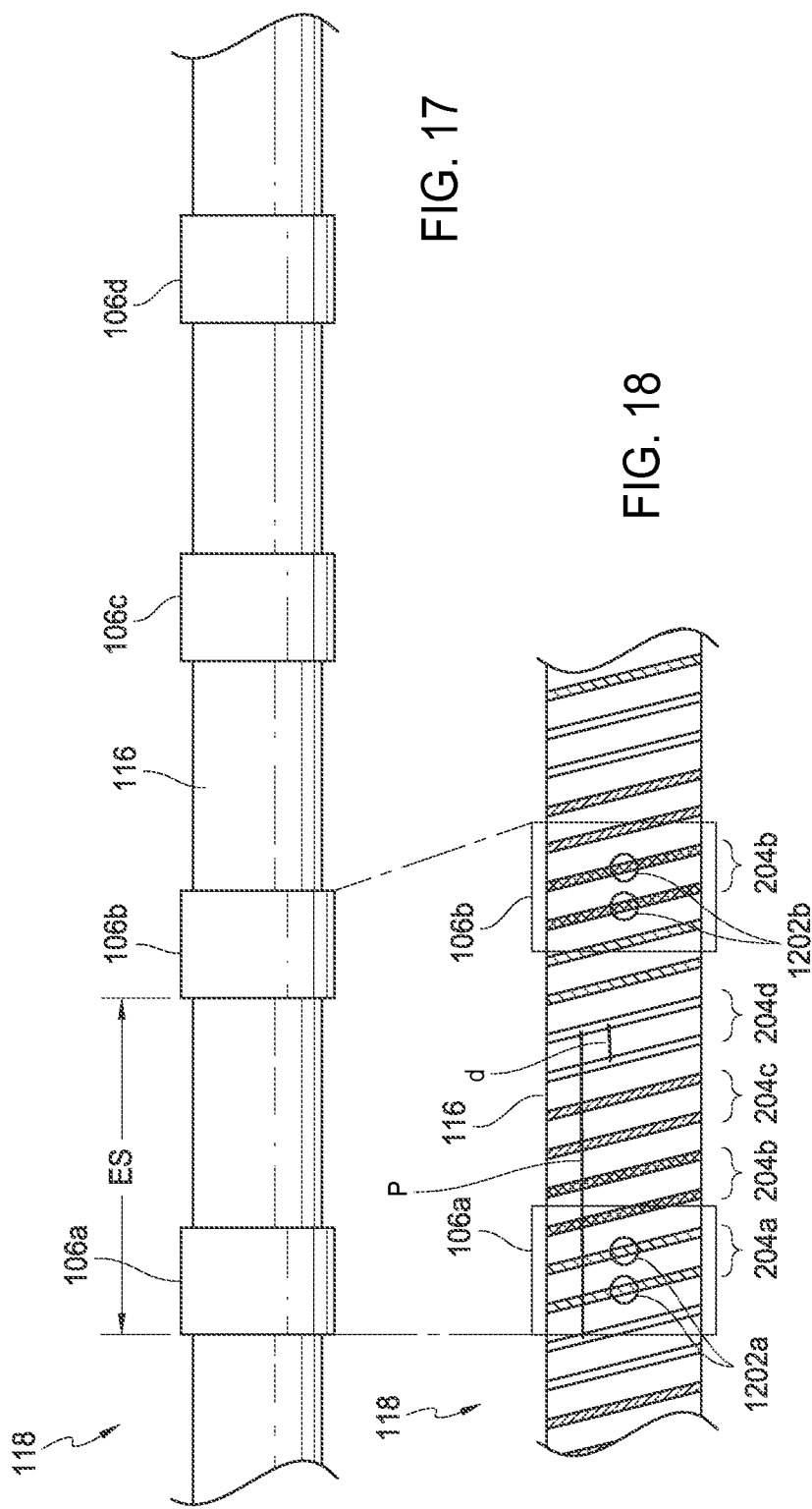

| Pattern | Steps |
|---|---|
| ABCDABCDABCDABCDABCDABCDABCDABCDABCDABCDABCDABCD | (2) |
| ABCDABCDABCDABCDABCDABCDABCDABCDABCDABCDABCDABCD | (10) |
| ABCDABCDABCDABCDABCDABCDABCDABCDABCDABCDABCDABCD | (18) |
| ABCDABCDABCDABCDABCDABCDABCDABCDABCDABCDABCDABCD | (26) |

FIG. 19

| Pattern | Steps |
|---|---|
| ABCDABCDABCDABCDABCDABCDABCDABCDABCDABCDABCDABCD | (6) |
| ABCDABCDABCDABCDABCDABCDABCDABCDABCDABCDABCDABCD | (14) |
| ABCDABCDABCDABCDABCDABCDABCDABCDABCDABCDABCDABCD | (22) |
| ABCDABCDABCDABCDABCDABCDABCDABCDABCDABCDABCDABCD | (30) |

FIG. 20

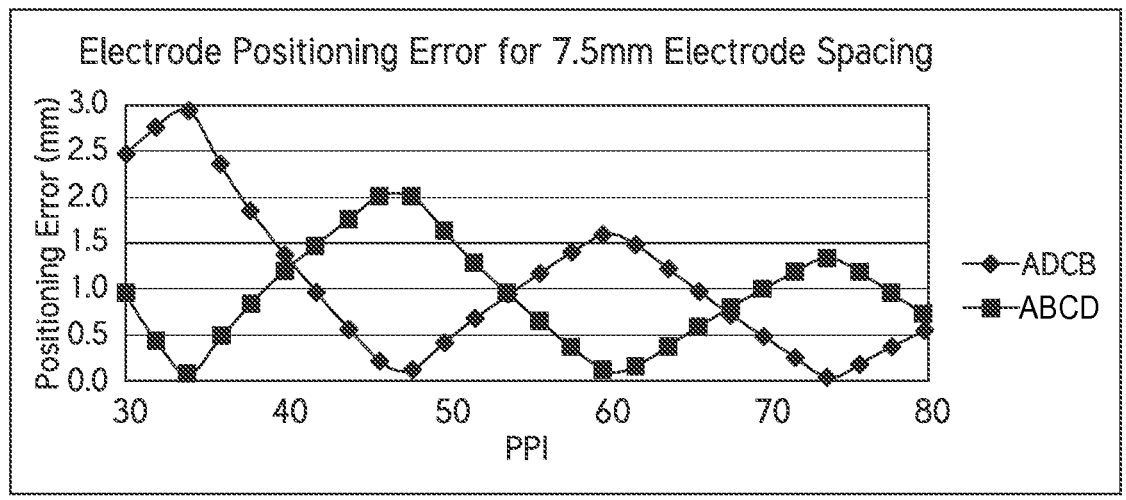

FIG. 21

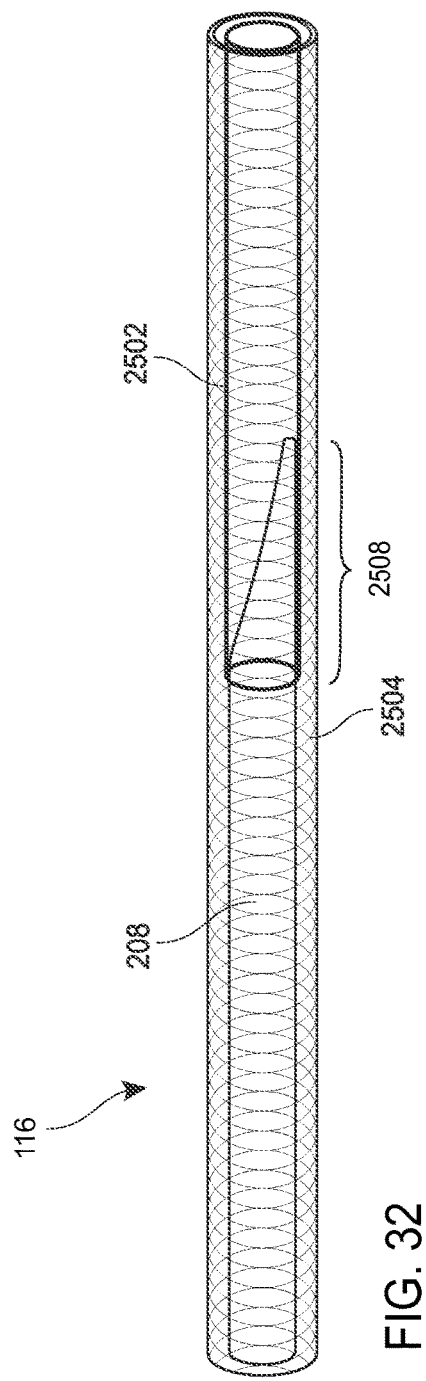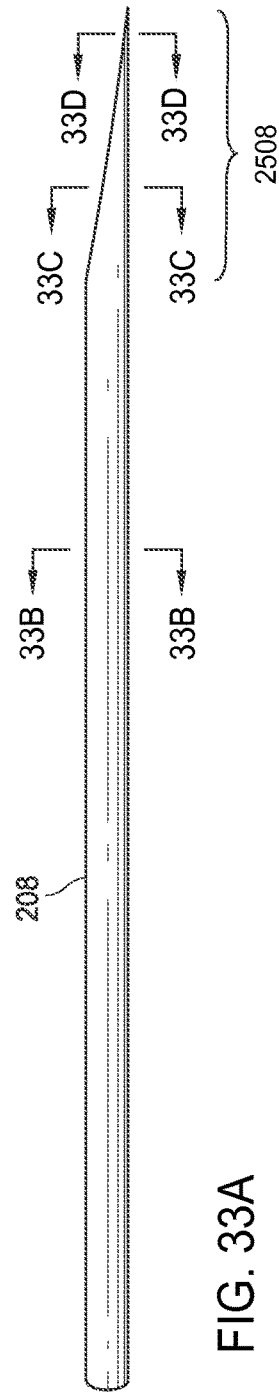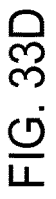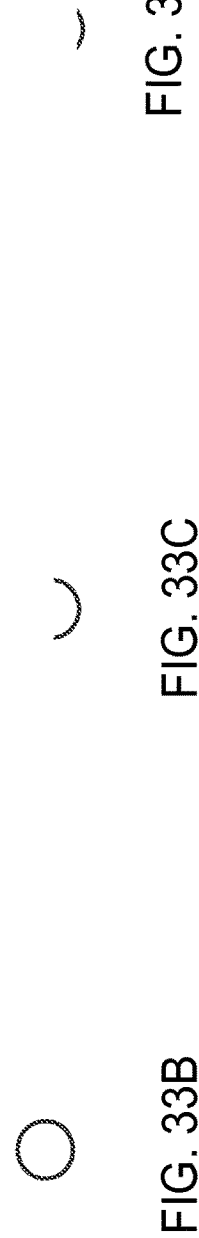
FIG. 32
FIG. 33A
FIG. 33B
FIG. 33C
FIG. 33D

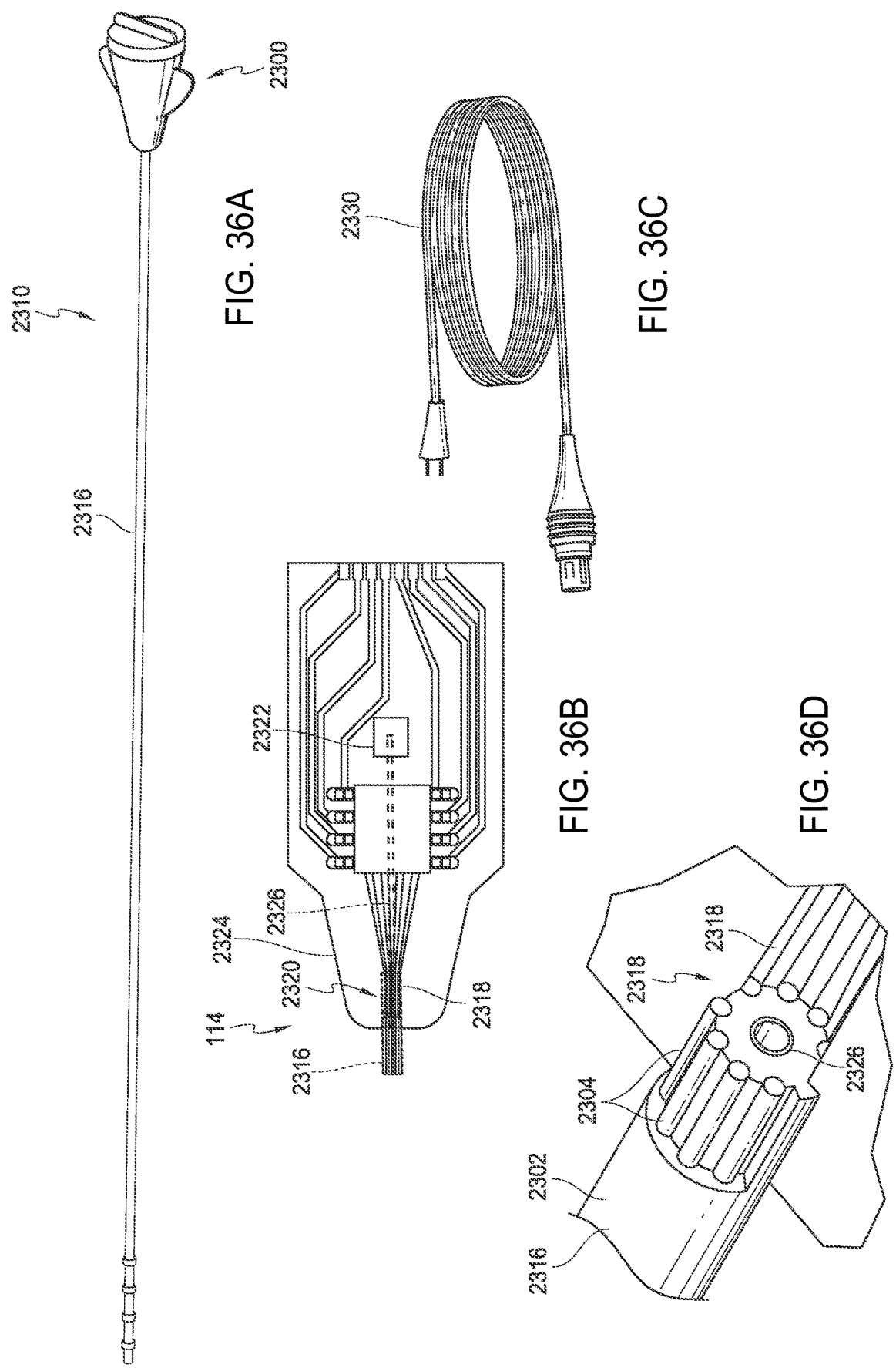

NEUROMODULATION CATHETERS AND ASSOCIATED SYSTEMS AND METHODS

CROSS-REFERENCE TO RELATED APPLICATIONS

This application claims the benefit of U.S. Provisional Patent Application No. 61/983,812, filed Apr. 24, 2014, which is incorporated herein by reference in its entirety.

TECHNICAL FIELD

The present technology relates generally to neuromodulation devices and methods of deployment. Some embodiments, for example, are directed to neuromodulation catheters (e.g., having braided shafts) and associated methods of use and manufacture.

BACKGROUND

The sympathetic nervous system (SNS) is a primarily involuntary bodily control system typically associated with stress responses. SNS fibers that innervate tissue are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiologies of hypertension, states of volume overload (such as heart failure), and progressive renal disease.

Sympathetic nerves innervating the kidneys terminate in the blood vessels, the juxtaglomerular apparatus, and the renal tubules. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone and likely contribute to increased blood pressure in hypertensive patients. For example, reduced renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

Recently, neuromodulation devices have been developed that may reduce sympathetic nerve activity by applying an energy field to a target site in the renal blood vessel (e.g., via radio frequency ablation) and may thereby reduce blood pressure in patients with treatment-resistant hypertension. A number of neuromodulation devices utilize one or more thermocouples ("TC") to measure temperature at or near an electrode. The presence of TC wires within the catheter shaft, particularly in neuromodulation devices having two or more electrodes, can make the shaft bulky, stiff, and/or relatively expensive to manufacture.

BRIEF DESCRIPTION OF THE DRAWINGS

Many aspects of the present technology can be better understood with reference to the following drawings. Furthermore, components can be shown as transparent in certain views for clarity of illustration only and not to indicate that the illustrated component is necessarily transparent. The components in the drawings are not necessarily to scale. Instead, emphasis is placed on illustrating clearly the principles of the present technology.

FIG. 2A is a side view of the catheter shown in FIG. 1A in a low-profile configuration in accordance with the present technology.

FIGS. 2B and 2C are enlarged views of a portion of a shaft of the catheter shown in FIG. 2A.

FIG. 9 is an end view showing an axial profile of a shaft in an expanded configuration, the shaft configured in accordance with the present technology.

FIGS. 10-12 are schematic end views showing various axial profiles of shafts, each in an expanded configuration and configured in accordance with the present technology.

FIG. 17 is a side view of the distal portion of a shaft in a low-profile or delivery configuration showing an electrode spacing, the shaft configured in accordance with the present technology.

FIG. 18 is a schematic representation of an electrode placement pattern for a portion of the shaft shown in FIG. 17.

FIG. 19 is a table showing ABCD-patterned electrode spacing arrangements configured in accordance with an embodiment of the present technology.

FIG. 20 is a table showing ADCB-patterned electrode spacing arrangements configured in accordance with an embodiment of the present technology.

FIG. 21 is a graph showing picks per inch ("PPI") versus electrode positioning error for an electrode spacing of 7.5 mm.

FIG. 32 is a side view of a shaft having an over-the-wire configuration, the shaft configured in accordance with an embodiment of the present technology.

FIG. 33A is an enlarged, isolated side view of a first elongated member of the shaft shown in FIG. 32.

FIGS. 33B-33D are cross-sectional end views taken along lines 33B-33B, 33C-33C and 33D-33D in FIG. 33A, respectively.

FIG. 36A is a perspective view of a portion of a catheter configured in accordance with another embodiment of the present technology.

FIG. 36B is a perspective, enlarged view of a proximal portion of the catheter shown in FIG. 36A.

FIG. 36C is a perspective view of a connector for use with the catheter shown in FIG. 36A.

FIG. 36D is a perspective, enlarged view of a proximal portion of the catheter shown in FIG. 36A.

DETAILED DESCRIPTION

The present technology is directed to devices and methods for deployment and positioning of neuromodulation devices. Some embodiments of the present technology, for example, are directed to neuromodulation catheters having braided shafts and associated systems and methods. In certain embodiments, the neuromodulation catheters may have braided shafts. Specific details of several embodiments of the technology are described below with reference to FIGS. 1A-37B. Although many of the embodiments are described below with respect to systems, devices, and methods for renal neuromodulation, other applications (e.g., neuromodulation of other non-renal nerves, treatments other than neuromodulation, etc.) and other embodiments in addition to those described herein are within the scope of the technology. Additionally, several other embodiments of the technology can have different configurations, components, or procedures than those described herein. For example, although the present technology is illustrated and explained with respect to a four-electrode catheter, catheters having more or fewer than four electrodes are also within the scope of the technology (e.g., one, two, three, five, etc.). A person of ordinary skill in the art, therefore, will accordingly understand that the technology can have other embodiments with additional elements, or the technology can have other embodiments without several of the features shown and described below with reference to FIGS. 1A-37B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. SYSTEM OVERVIEW

Figure 1B:
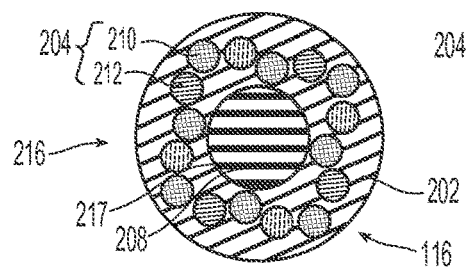
FIG. 1B is a cross-sectional end view of the catheter shaft in FIG. 1A taken along line 1B-1B.
Figure 1C:
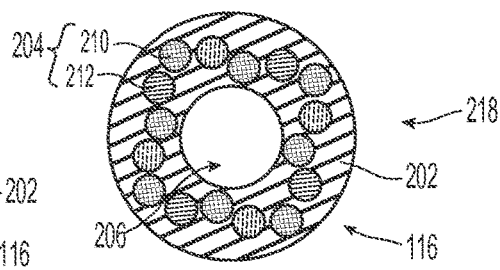
FIG. 1C is a cross-sectional end view of the catheter shaft in FIG. 1A taken along line 1C-1C.
Figure 1A:
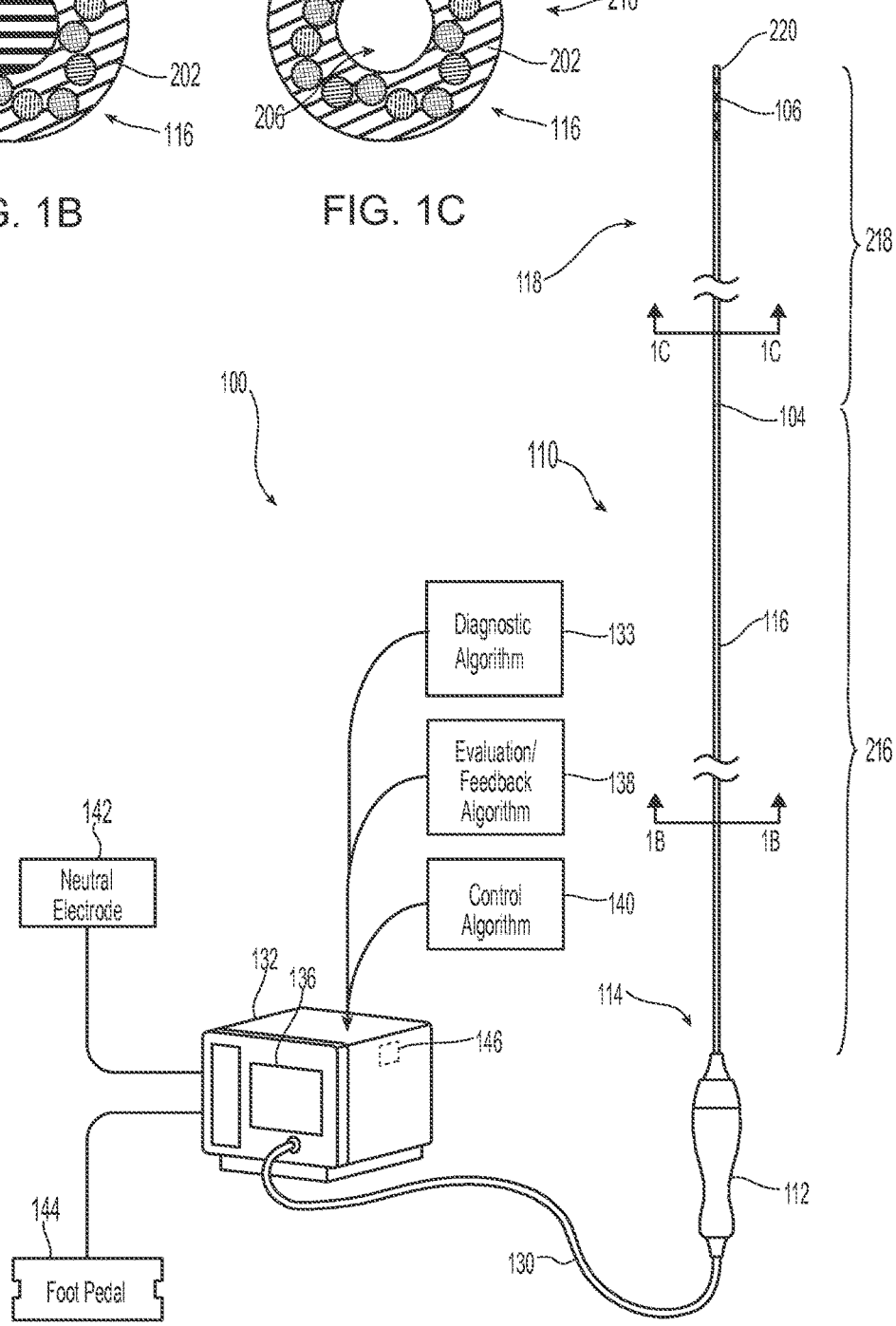
FIG. 1A is a partially schematic illustration of a neuromodulation system configured in accordance with an embodiment of the present technology.
Figure 3:
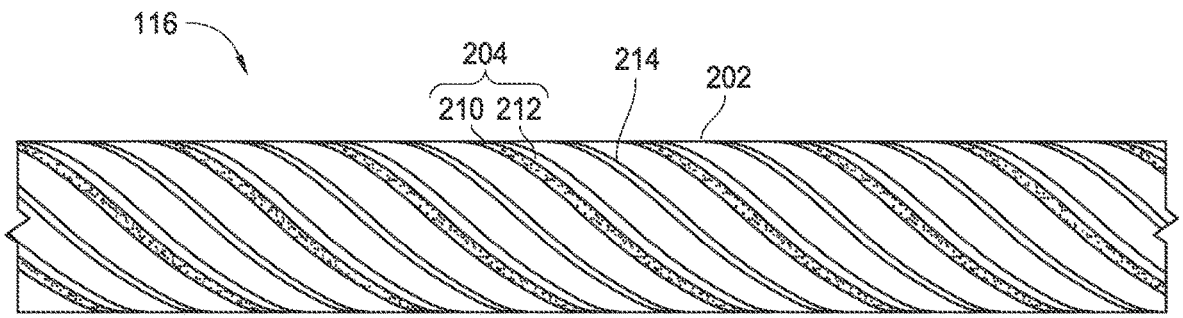
FIG. 3 is an enlarged side view of a portion of the shaft having TC assemblies and braiding element(s) wrapped in the same direction, the shaft configured in accordance with several embodiments of the present technology.
Figure 4:
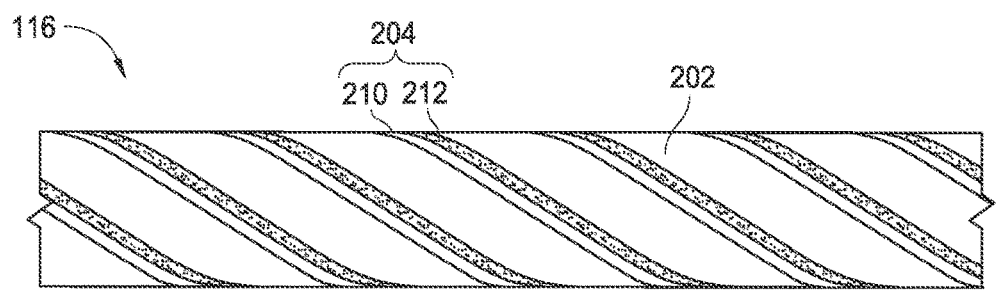
FIG. 4 is an enlarged side view of a portion of the shaft having a braid that only includes TC assemblies (and not braiding elements), the shaft configured in accordance with several embodiments of the present technology.

FIG. 1A is a partially-schematic perspective view of a neuromodulation system 100 ("system 100") configured in accordance with an embodiment of the present technology. The system 100 includes an intravascular catheter 110 operably coupled to an energy source or energy generator 132 via a connector 130 (e.g., a cable). The catheter 110 can include an elongated shaft 116 having a proximal portion 114 and a distal portion 118 carrying one or more electrodes 106. The catheter 110 also includes a handle assembly 112 at the proximal portion 114. The elongated shaft 116 is configured to intravascularly locate the distal portion 118 at a treatment location within a renal blood vessel or within another suitable body lumen (e.g., within a ureter) of a human patient. As shown in the cross-sectional end views of the shaft 116 in FIGS. 1B and 1C, the shaft 116 can be a flexible, tubular structure composed of a polymer jacket 202 and a plurality of TC assemblies 204 at least partially embedded within the polymer jacket 202. A distal portion of each of the TC assemblies 204 can be electrically coupled to a corresponding electrode 106. As such, the TC assemblies 204 may extend along the length of the shaft 116 and provide an electrical connection between the handle assembly 112 and the electrodes 106 at the distal portion 118 of the shaft 116. The structure and composition of the shaft 116 is discussed in greater detail below with reference to FIGS. 2A-37D.

The shaft 116 can further include a rapid-exchange ("RX") port 104 ("port 104") configured to receive a guidewire (not shown) therethrough. As shown in FIG. 1A, the shaft 116 can include a first section 216 extending from the handle 112 to the port 104, and a second section 218 extending distally from the port 104 to a distal end 220 of the shaft 116. As shown in FIG. 1B, the first section 216 can be substantially solid throughout its cross-section (e.g., no central lumen). For example, the first section 216 can include a generally cylindrical elongated member 208, such as a mandrel, that comprises a central portion of the first section 216. The TC assemblies 204 may be wrapped about the elongated member 208. The elongated member 208 can extend from the proximal portion 114 of the shaft 116 to the port 104. As shown in FIG. 1B, an outer circumference 217 of the elongated member 208 can abut an inner surface of the polymer jacket 202. Such a configuration may reduce the profile of the shaft 116, improve rotational force transmission along the shaft 116 when a rotational force is applied to the proximal portion 114 of the shaft (e.g., by the handle 112), and/or improve axial strength of the shaft 116. In some embodiments, the first section 216 can include an elongated member having other shapes and configurations and/or can be filled with one or more materials (e.g., a polymer filling). In certain embodiments, such as those including a catheter 110 configured to receive a guidewire via an over-the-wire ("OTW") approach, the first section 216 can have at least one lumen instead of or in addition to an elongated member. Further details regarding catheter designs to accommodate RX and OTW configurations are discussed below with reference to FIGS. 22-34.

As shown in FIG. 1C, the second section 218 can have a lumen 206 that extends from the port 104 to the distal end 220 of the shaft 116. The lumen 206 can be configured to receive a guidewire therethrough. In some embodiments, a liner (e.g., a polymer liner) (not shown) can be formed on the inner surface of the polymer jacket 202 to limit the likelihood of the guidewire (not shown) penetrating the polymer jacket 202 and disrupting the TC assemblies 204.

In some embodiments, the outer diameter of the second section 218 can be larger than the outer diameter of the first section 216 (for example, to accommodate a guidewire). In such embodiments, the elongated shaft 116 can have a tapered shape in a proximal direction and/or include a gradual or abrupt step up in outer diameter between the first and second sections 216, 218. In other embodiments, the second section 218 can have an outer diameter that is smaller than or equal to the outer diameter of the first section 216.

Referring back to FIG. 1A, the energy generator 132 can be configured to generate a selected form and/or magnitude of energy for delivery to the treatment site via the electrodes 106. For example, in a particular embodiment, the energy generator 132 can include an energy source (not shown) operably coupled to one or more electrodes 106 and configured to generate radiofrequency (RF) energy (monopolar or bipolar). In some embodiments, the RF energy may be pulsed RF energy. In other embodiments, however, the energy generator 132 may be configured to generate microwave energy, optical energy, ultrasound energy (e.g., intravascularly delivered ultrasound, high-intensity focused ultrasound (HIFU)), direct heat energy, radiation (e.g., infrared, visible, gamma), or another suitable type of energy.

The energy generator 132 may also be configured to control, monitor, supply, or otherwise support operation of the catheter 110. For example, a control mechanism, such as foot pedal 144, may be connected (e.g., pneumatically connected or electrically connected) to the energy generator 132 to allow an operator to initiate, terminate and/or adjust various operational characteristics of the energy generator, such as power delivery. In some embodiments, for example, the energy generator 132 may be configured to provide delivery of a monopolar electric field via the electrode(s) 106. In such embodiments, a neutral or dispersive electrode 142 may be electrically connected to the energy generator 132 and attached to the exterior of the patient (not shown). In some embodiments, instead of or in addition to the electrodes 106, the distal portion 118 of the elongated shaft 116 can have ports or other substance delivery features to produce chemically based neuromodulation by delivering one or more chemicals. For example, suitable chemicals include guanethidine, ethanol, phenol, a neurotoxin (e.g., vincristine), or other suitable agents selected to alter, damage, or disrupt nerves. In certain embodiments, a combination of chemicals may be used.

In some embodiments, the system 100 includes a remote control device (not shown) configured to be sterilized to facilitate its use within a sterile field. The remote control device can be configured to control operation of the electrodes 106, the energy generator 132, and/or other suitable components of the system 100. For example, the remote control device can be configured to allow for selective activation of the electrodes 106. In other embodiments, the remote control device may be omitted and its functionality may be incorporated into the handle 112 or energy generator 132.

As shown in FIG. 1A, the energy generator 132 can further include an indicator or display screen 136. The energy generator 132 can include other indicators, including one or more LEDs, a device configured to produce an audible indication, and/or other suitable communicative devices. In the embodiment shown in FIG. 1A, for example, the display 136 includes a user interface configured to receive information or instructions from a user and/or provide feedback to the user. For example, the energy generator 132 can be configured to provide feedback to an operator before, during, and/or after a treatment procedure via the display 136. The feedback can be based on output from one or sensors (not shown) associated with the distal portion 118 of the elongated shaft 116 such as temperature sensor(s), impedance sensor(s), current sensor(s), voltage sensor(s), flow sensor(s), chemical sensor(s), ultrasound sensor(s), optical sensor(s), pressure sensor(s) and/or other sensing devices.

The system 100 can further include a controller 146 having, for example, memory (not shown) and processing circuitry (not shown). The memory and storage devices are computer-readable storage media that may be encoded with non-transitory, computer-executable instructions such as diagnostic algorithm(s) 133, evaluation/feedback algorithm(s) 138, and/or control algorithm(s) 140. The control algorithms 140 can be executed on a processor (not shown) of the system 100 to control energy delivery to the electrode(s) 106. In some embodiments, selection of one or more parameters of an automated control algorithm 140 for a particular patient may be guided by diagnostic algorithm(s) 133 that measure and evaluate one or more operating parameters prior to energy delivery. The diagnostic algorithm(s) 133 provide patient-specific feedback to the clinician prior to activating the electrode(s) 106 that can be used to select an appropriate control algorithm 140 and/or modify the control algorithm 140 to increase the likelihood of efficacious neuromodulation.

Although the controller 146 is incorporated into the energy generator 132 in the embodiment shown in FIG. 1A, in other embodiments the controller 146 may be an entity distinct from the energy generator 132. For example, additionally or alternatively, the controller 146 can be a personal computer(s), server computer(s), handheld or laptop device(s), multiprocessor system(s), microprocessor-based system(s), programmable consumer electronic(s), digital camera(s), network PC(s), minicomputer(s), mainframe computer(s), and/or any suitable computing environment.

II. SELECT EMBODIMENTS OF CATHETER DEVICES

A. Elongated Shaft Composition and Structure

FIG. 2A is a side view of the catheter 110 with the distal portion 118 of the shaft 116 in a low-profile or delivery state, and FIGS. 2B and 2C are enlarged views of various portions of the elongated shaft 116 shown in FIG. 2A. Referring to FIGS. 2A-2C together, the shaft 116 can be an elongated tubular member formed of a braid 205 at least partially embedded within a polymer jacket 202. The braid 205, for example, can include four TC assemblies 204 (labeled individually as TC assemblies 204a-d) intertwined with a braiding element 214. Although the braid 205 is shown having five components in FIGS. 2A-2C (four TC assemblies 204 and one braiding element 214), in some embodiments the braid 205 can have more or fewer than five components. A proximal portion of each TC assembly 204a-d is electrically connected to the handle 112 (described in greater detail below with reference to FIGS. 35A-37B), and a distal portion of each TC assembly 204a-d is electrically connected to a corresponding electrode 106a-d carried by the shaft 116 (described in greater detail below with reference to FIGS. 13-21). As such, the TC assemblies 204a-d are individually configured to measure temperature at or near its corresponding electrode 106a-d.

Each TC assembly 204a-d can include a first wire 210 (labeled individually 210a-d) and a second wire 212 (labeled individually 212a-d) made of dissimilar metals. As best seen in FIG. 2B, the first and second wires 210a-d, 212a-d can wrap around a circumference of the shaft 116 and can be arranged generally parallel to one another. Each TC assembly 204a-d can be physically and electrically isolated from the other TC assemblies 204a-d along the elongated shaft 116 between the proximal portion and the distal portion. In some embodiments, the first wires 210a-d can be made of constantan and the second wires 212a-d can be made of copper (or vice versa) such that each TC assembly 204 is configured to form a T-type thermocouple. In other embodiments, however, other types of thermocouples may be used and/or the first and/or second wires 210, 212 may be composed of other materials. Although the braid 205 is shown having four TC assemblies 204a-d, in other embodiments the braid 205 can include more or fewer than four TC assemblies (e.g., one, two, three, five, etc.).

Although the braid 205 is shown having a single braiding element 214, in other embodiments the braid 205 can include more than one braiding element (e.g., two, three, five, etc.) having the same or different size and/or or structure, and/or made of the same or different materials. In some embodiments, the braid 205 may not include any braiding element. The braiding element 214 can comprise a polymer material, such as a monofilament polymer strand or a multifilament polymer strand. Additionally, the braiding element 214 may comprise a metal. For example, the braiding element 214 can be a metal or other material having shape-memory properties corresponding to temperature thresholds (e.g., polyethylene terephthalate (PET), polyethylene naphthalate (PEN), PEN-PET, etc.). As discussed in further detail below with reference to FIGS. 5-8, all or a portion of the braiding element 214 can be heat set to a desired shape (e.g., a helical/spiral configuration) such that the braiding element is configured to impart a desired expanded configuration upon the elongated shaft 116 and/or enhance the spiral/helical memory of the shaft.

As shown in FIG. 2B, the braiding element 214 and the TC assemblies 204a-d can be intertwined and/or braided together along the length of the shaft 116. The braiding element 214 can be positioned above 230 and below 232 the adjacent TC wire 210/212 at alternating intersections between the TC wire 210/212 and the braiding element 214. For example, the braiding element 214 and the first wire 210d can have a "2 under, 2 over" configuration whereby the braiding element 214 crosses the first wire 210d on the radially interior side of the first wire 210 ("under") at two successive intersections, crosses on the radially exterior side of the second wire ("over") at the following two successive intersections, and continues this pattern for all or a portion of the length of the shaft 116. In other embodiments, the braiding element 214 may be arranged to cross over one or both wires 210, 212, cross under one or both wires 210, 212, and/or cross according to other patterns (e.g., "1 over, 1 under," "3 over, 3 under," etc.). Additionally, the braiding element 214 and the TC assemblies 204a-d can wrap around the shaft 116 in opposing directions (FIG. 2B) or the same direction (see, for example, FIG. 3). In some embodiments, the TC assemblies 204a-d and the braiding element 214 wrap around the shaft 116 but do not cross over the longitudinal axis of one another (see, for example, FIG. 3). In yet other embodiments, the shaft 116 does not include any braiding element and the shaft 116 comprises only the polymer jacket 202 and the TC assemblies 204 (see, for example, FIG. 4). A person of ordinary skill in the art will understand that the shaft 116 can have other configurations and/or can include additional or fewer braid 205 components.

Referring still to FIG. 2B, the braid 205 can have a pitch P (i.e., the longitudinal distance required for one revolution of a given TC assembly 204a-d) that can be generally constant along the length of the shaft 116. In other embodiments, the pitch P can be vary along the length of the shaft 116. For example, the braid 205 can have a tighter pitch P at a distal region of the shaft 116 for increased flexibility, and a wider pitch P at a proximal region for increased rigidity. Likewise, the PPI of the shaft 116 (i.e., longitudinal distance between successive wires) can be similarly selected to impart desired flexibility and/or rigidity along at least a portion of the shaft 116. As discussed in greater detail below with reference to FIGS. 17-22, the braid pitch P can be selected to achieve a desired spacing between adjacent electrodes along the shaft 116.

Figure 5A:
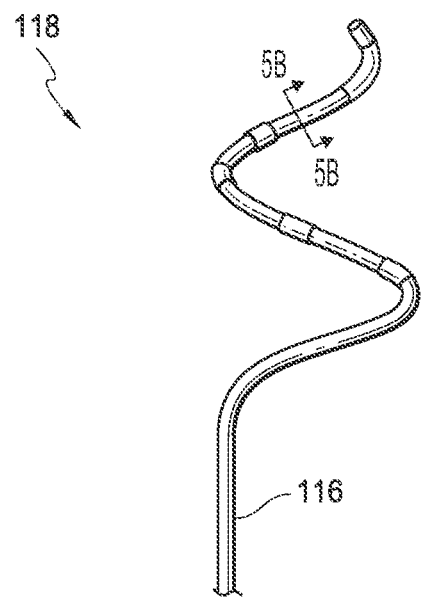
FIG. 5A is a side view of a distal portion of the shaft in an expanded configuration, the shaft configured in accordance with an embodiment of the present technology.
Figure 5B:
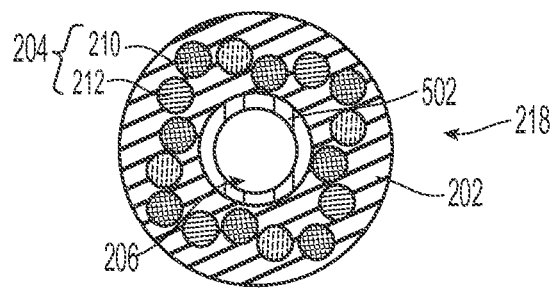
FIG. 5B is a cross-sectional end view of the distal portion of the shaft taken along line 5B-5B in FIG. 5A.
Figure 6:
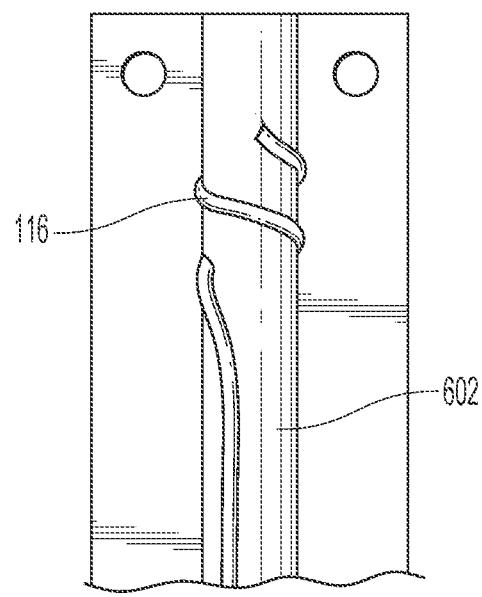
FIG. 6 is a side view of the distal portion of the shaft on a mandrel during a stage of manufacturing in accordance with an embodiment of the present technology.

FIG. 5A is a side view of the distal portion 118 of the shaft 116 in an expanded or deployed configuration, and FIG. 5B is a cross-sectional end view taken along line 5B-5B in FIG. 5A. Referring to FIGS. 5A-5B together, in the expanded or deployed configuration, the distal portion 118 of the shaft 116 can have a generally helical/spiral shape. The distal portion 118 of the shaft 116 can include a tubular, elongated shape-memory core (e.g., Nitinol) 502 disposed within the lumen 206 of the polymer jacket 202. During manufacturing, the core 502 can be heat set on a mandrel 602 after being assembled into the shaft 116, or in other embodiments (not shown), the core can be heat set prior to placement within the lumen 206.

Figure 7:
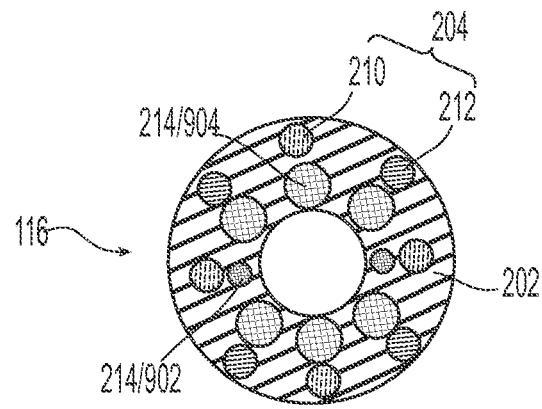
FIGS. 7-8 are cross-sectional end views of a shaft showing various braid configurations, the braid configured in accordance with the present technology.
Figure 8:
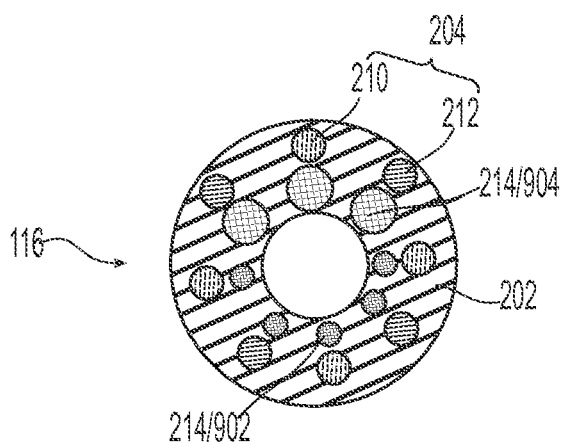

Instead of or in addition to the core 502, the braid 205 can include one or more braiding element(s) 214 composed of a shape-memory material such as Nitinol, polymer strands with a glass transition temperature greater than about 60° C., and the like. The positioning, cross-sectional area and/or composition of any or all of the braid 205 components can be manipulated to impart a desired helical/spiral shape on the expanded distal section 118. For example, in some embodiments the shaft 116 can include a mixture of large and small braiding element(s) 214. As shown in FIG. 7, the shaft 116 can include a plurality of large braiding elements 904 having a first grouping positioned on one side of the shaft 116 and a second grouping positioned on the opposite side of the shaft 116. The smaller braiding elements 902 can be positioned between the two groupings. As shown in FIG. 8, in some embodiments the shaft 116 can include a grouping of large braiding elements 904 positioned on one side of the shaft 116 and a grouping of small braiding elements 902 positioned on the opposite side of the shaft 116. In other embodiments, the shaft 116 can include other patterns and/or configurations of braiding elements 214. Likewise, the shaft 116 can include multiple braiding elements 214 made of the same or different materials.

FIG. 9 is a schematic, axial view of the shaft 116 in the expanded configuration showing the desired contact pattern (denoted by contact points c) between electrodes and the vessel wall (not shown). During energy delivery via the electrodes, it can be advantageous to have the electrodes positioned on the shaft 116 such that, when the distal portion 118 is in the helical/spiral expanded configuration, the electrodes are evenly distributed about the circumference of the helix/spiral shape and therefore evenly distributed about the circumference of the vessel. In some embodiments, it can be advantageous to have each electrode 106 in a separate quadrant. Moreover, as shown in FIGS. 10-11, in some embodiments the shaft 116 can include one or more bumps 1000 protruding radially outwardly from the circumference of the shaft 116. The bumps 1000 can correspond to the contact points c and increase the contact force between the electrodes and the vessel wall.

B. Electrodes

1. Electrode Connectivity

Figure 13:
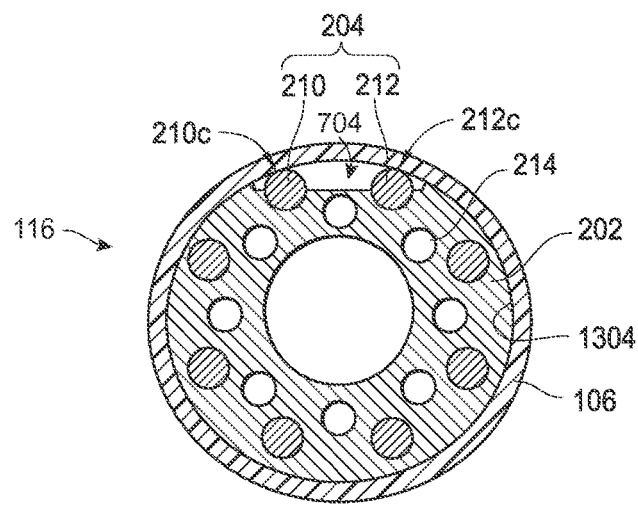
FIG. 13 is a cross-sectional end view of the shaft shown in FIG. 2C taken along line 13-13.

FIG. 13 is a cross-sectional end view of the shaft 116 in FIG. 2C taken along line 13-13. Referring to FIGS. 2B and 13 together, the electrodes 106 can be separate band electrodes (labeled individually as electrodes 106a-d) axially spaced apart along the distal portion 118 of the shaft 116. The body of each electrode 106-d surrounds the shaft 116 and at least a portion of an inner surface 1304 of each electrode 106a-d contacts the polymer jacket 202. Additionally, at least a portion of each electrode 106a-d contacts its corresponding TC assembly 204a-d (e.g., at 210c and 212c, respectively). For example, if TC assembly 204a corresponds to electrode 106a, an inner surface 1304 of the electrode 106a contacts at least a portion of each of the first and second wires 210a, 212a. Because the first and second wires 210, 212 run parallel to each other and are separated by a generally constant distance along their lengths, the portion of the first wire 210 in contact with the electrode 106 can be separated from the portion of the second wire 212 in contact with the electrode 106 along the inner surface 1304 of the electrode 106. Typical thermocouples require a junction between the two wires at the measuring end of the thermocouple. The electrode 106 (which may comprise one or more metals such as gold) may be used to efficiently transfer current between two separated wire contacts. As such, the distance between the wires 210, 212 may have a negligible effect on the accuracy of the measured temperature. As a result, the first and second wires 210, 212 can be configured to measure a temperature at or near the electrode 106.

Figure 14:
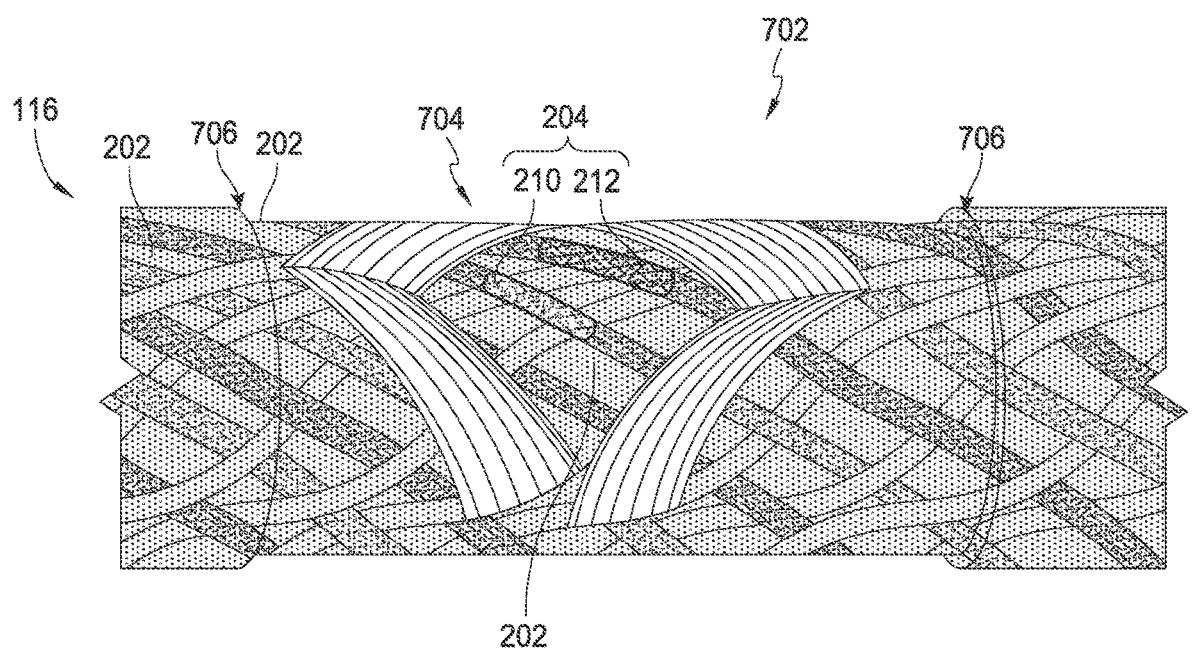
FIG. 14 is an enlarged, side perspective view of the shaft shown in FIG. 2B with the electrode removed for purposes of illustration.
Figure 15:
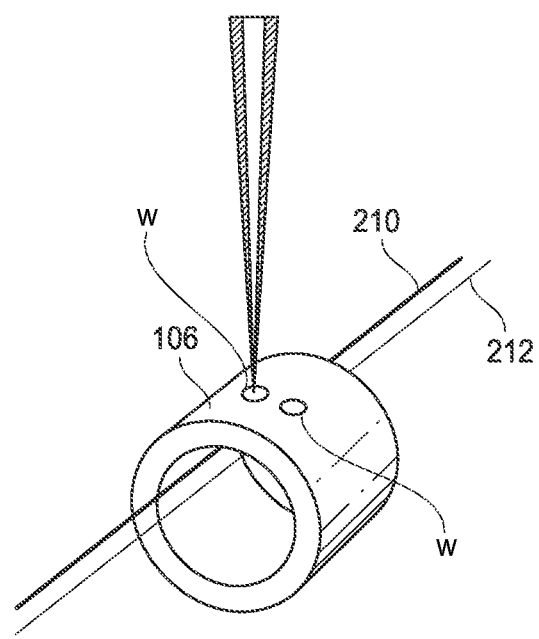
FIG. 15 is a schematic representation depicting the welding of an electrode to a TC assembly in accordance with an embodiment of the present technology.

FIG. 14 shows a portion of the shaft 116 with the electrode 106 removed for purposes of illustration. To optimize contact between the electrode 106 and the TC assemblies 204, the shaft 116 can include a notch 702 extending around its circumference that corresponds to the placement of the electrode 106. During manufacturing an additional portion of the polymer jacket 202 within the notch 702 can be removed (e.g., via laser ablation or other suitable methods) to form a recessed portion 704. As shown in FIG. 14, the recessed portion 704 can form a diamond shaped groove within a portion of the notch 702 that exposes a portion of the first and second wires 210, 212 of the targeted TC assembly 204a-d. As such, within the recessed portion 704, the polymer jacket 202 can surround a radially interior portion of the wires 210, 212 such that the polymer jacket 202 intersects the body of the wires 210, 212 at the exposed portions. In the embodiment shown in FIGS. 13 and 14, the recessed portion 704 extends toward the interior of the polymer jacket 202 to a radial distance (measured from the center of the lumen 206) generally equivalent to the radial distance between the center of one or both the wires 210, 212 and the center of the lumen 206.

It will be appreciated that the notch 702 and/or recessed portion 704 can have other shapes and/or configurations. For example, in some embodiments the notch 702 can extend around only a portion of the circumference of the shaft 116. In the embodiment shown in FIG. 14, a periphery 706 of the notch 702 is generally linear. In other embodiments, at least a portion of the periphery 706 of the notch 702 can be non-linear (e.g., sinusoidal, zig-zag, etc.). In certain embodiments, the shaft 116 does not have any notches and the recessed portion 704 is formed on the exterior surface of the shaft 116. Moreover, the recessed portion 704 can be formed in any suitable shape (e.g., circle, square, star-shaped, etc.).

To electrically couple the individual electrodes 106a-d to their respective TC assemblies 204a-d, each electrode 106a-d can be placed around the shaft 116 and positioned within its respective notch 704. All or a portion of the electrode 106 can then be swaged such that an inner surface 1304 of the electrode 106 is urged nearer and/or forced into contact with the exposed portions of the first and second wires 210, 212. As shown schematically in FIG. 15, once properly positioned and swaged, each electrode 106 can be welded to the corresponding exposed portions of the wires 210, 212 at weld points w. In other embodiments, however, other suitable techniques may be used to couple the electrodes 106 to wires 210, 212. As discussed in greater detail below, in some embodiments it may be advantageous to perform the welding at a generally central location on the electrode 106 to avoid deterioration of the electrode material at the periphery.

Figure 16:
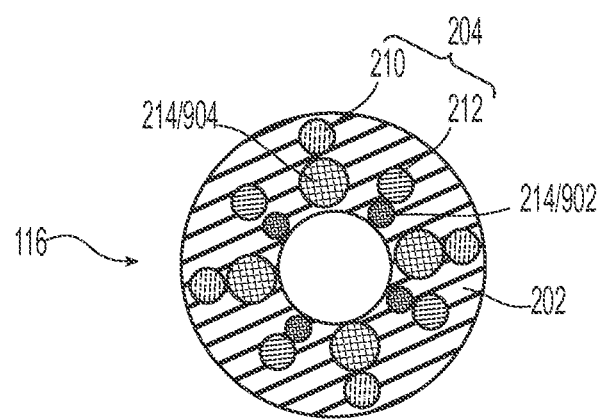
FIG. 16 is a cross-sectional end view of a shaft having braiding elements with varying cross-sectional areas configured in accordance with an embodiment of the present technology.

Several techniques can be utilized to enhance the electrical and/or mechanical connection between the electrodes 106 and the wires 210, 212. For example, to enhance the bond between the inner surface of the electrode 106 and the first and second wires 210, 212, a conductive filler (not shown) may be injected into the recessed portion 704 instead of or in addition to welding. Also, to increase the surface contact between the electrodes and the first and second wires 210, 212, the positioning, cross-sectional area and/or composition of any or all of the braid 205 components can be manipulated to selectively position the wires 210, 212 near the outer surface of the polymer jacket 202. For example, the diameter of the braiding element 214 and the positioning of the braiding element 214 (relative to the first and/or second wires 210, 212) can be selected to affect the positioning of the first and/or second wires 210, 212. As shown in FIG. 16, for example, the shaft 116 can include at least one braiding element 214 having a larger cross-sectional area 904 positioned radially inferior to the first wire 210 and/or second wire 212. The larger braiding element 904 is expected to help position the first and/or second wires 210, 212 closer to an outer surface of the polymer jacket 202. In a similar fashion, the selection of a monofilament or multifilament braiding element can affect electrode positioning. Likewise, braiding elements having circular cross-sectional areas can urge the first and/or second wires 210, 212 radially outwardly, while braiding elements having flattened cross-sectional areas (e.g., rectangle, ellipsis, etc.) may take up less radial space in the polymer jacket 202. Any or the above-referenced techniques can be utilized in any combination.

2. Electrode Spacing Algorithms

For efficacious treatment, it can be advantageous to create a fully-circumferential lesion along a length of the target blood vessel. For example, distal portion 118 can be configured to form a lesion or series of lesions (e.g., a helical/spiral lesion or a discontinuous lesion) that is fully-circumferential overall, but generally non-circumferential at longitudinal segments of the treatment location. As discussed above with reference to FIG. 2A and FIG. 9, the electrodes 106 can be positioned along the distal portion 118 of the shaft 116 such that, when the shaft 116 is in the expanded configuration, the electrodes are evenly distributed about the circumference of the helix/spiral shape into four quadrants. As demonstrated by FIG. 17, the distance ES between adjacent electrodes along the shaft 116 can be selected to achieve such a circumferential distribution of electrodes in the expanded configuration. For example, for vessel diameters between about 3 mm and about 8 mm, the distance ES between adjacent electrodes along the shaft 116 can be about 7.5 mm. In other embodiments, however, the electrode spacing ES may vary.

Because of the braided and/or wrapped configuration of the wires 210, 212 along the length of the shaft 116, several parameters must be considered in order to achieve a desired electrode spacing ES. For example, the distance d between adjacent wires, the size of the band electrodes, and the welding parameters can affect the electrode spacing ES. To illustrate this concept, FIG. 18 shows a section of the distal portion 118 of the shaft 116 that includes first, second, third and fourth TC assemblies 204a-d wrapped around the shaft 116 and first and second electrodes 106a, 106b (shown schematically) welded to first and second TC assemblies at weld points 1202a and 1202b, respectively. If the distance d between adjacent wires is too small (i.e., the wires are wound very close together), the weld points of a particular electrode will be too close together and may overlap. If the distance d is too large (i.e., the wires are wound too far apart), one or both of the weld points may be too close to the perimeter of the electrode which can lead to a poor weld (e.g., not enough metal for the weld to be effective). Accordingly, it can be advantageous to have the weld points spaced apart at a central portion of the electrode, as shown in FIG. 18. Additionally, it can be advantageous to form the weld points in a single plane (e.g., for ease of manufacturing).

FIG. 19 is a table showing ABCD-patterned electrode spacing arrangements, and FIG. 20 is a table showing ADCB-patterned electrode spacing arrangements. The letters "A," "B," "C," and "D" each represent a corresponding TC assembly 204a-d shown in FIGS. 17 and 18, and each row illustrates a different spacing between TC assembly welding points. Because each TC assembly 204a-d can only be coupled to a single electrode, in each row only one of "A," "B," "C," and "D" are surrounded by a box (which denotes the portion of the TC assembly to be coupled to its corresponding electrode). The first row of FIG. 19, for example, denotes a configuration where the electrodes are welded to successive, immediately adjacent portions of TC assemblies 204a-d. In such a configuration, there are "two steps" between welding points (denoted by the far right column). "Two steps," as used herein, denotes one move from a TC assembly with weld points to the next TC assembly with weld points ("two steps" because each wire counts as a step, and each TC assembly can include two wires). In the second row of FIG. 19, the weld points skip the immediately adjacent TC assembly and are located instead on the next occurring TC assembly (10 steps). Such a pattern continues in the rest of FIG. 19 and FIG. 20.

Based on the steps shown in the exemplary ABCD and ADCB patterns in FIGS. 19 and 20, a desired braid density PPI ("picks per inch") can be determined by plugging the steps and desired distance d between electrodes into the following equations:

Electrode Positioning Error $E$=electrode spacing ES−(steps*$d$);

Distance $d$ between adjacent wires (in mm)=25.4/PPI mm; and

Electrode Positioning Error $E$=electrode spacing ES−(steps*(25.4/PPI mm)).

FIG. 21 is a graph showing PPI versus electrode position error E for an electrode spacing ES of 7.5 mm. As used herein with reference to FIG. 21, "error" refers to the absolute difference between the actual electrode spacing and the desired electrode spacing (e.g., 7.5 mm). On the graph shown in FIG. 21, for the ABCD pattern, the electrode positioning error E is lowest at around 34 PPI and 48 PPI, and for the ADCB pattern, at around 61 PPI and 74 PPI. Depending on the desired electrode spacing ES and the size of the electrodes, however, one or more of these PPI values may still be undesirable. For example, 34 PPI may still be result in distance between adjacent wires being too large, and 74 PPI may still result in the distance between adjacent wires being too small. Accordingly, in other embodiments, other suitable arrangements and/or spacings may be utilized.

C. Select Embodiments of Guidewire Accommodations

1. Rapid Exchange Port Embodiments

As discussed above with reference to FIGS. 1A-1C, the elongated shaft 116 can include a port 104 configured to receive a guidewire in a rapid-exchange configuration.

Figure 22:
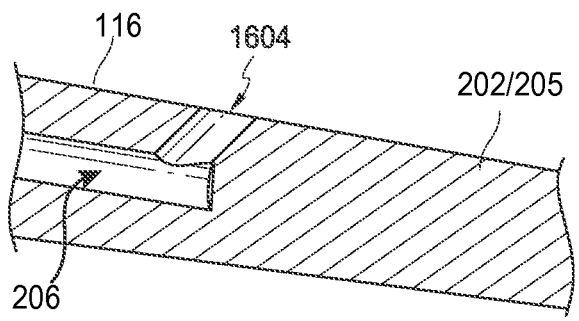
FIGS. 22-23 are side views of a shaft shown during various stages of manufacturing a rapid exchange port configured in accordance with an embodiment of the present technology.
Figure 23:
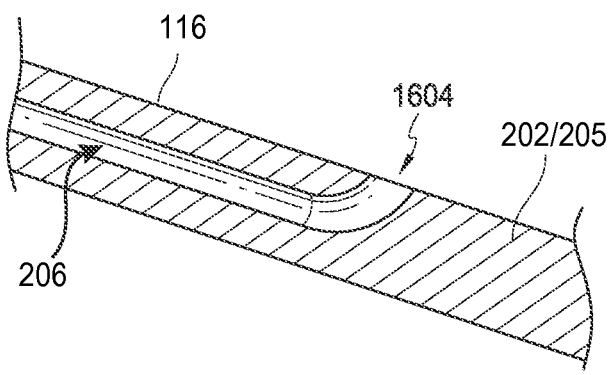
Figure 24:
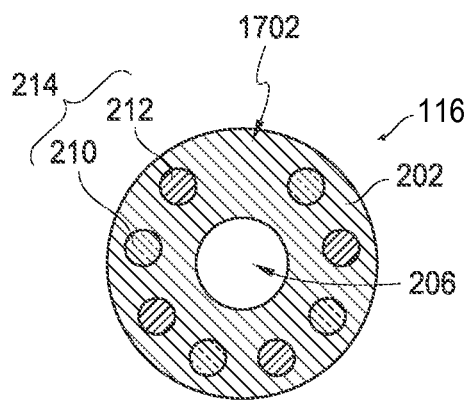
FIG. 24 is a cross-sectional end view of a shaft having a port section configured in accordance with an embodiment of the present technology.

Referring now to FIG. 22, the lumen 206 of the shaft 116 can have an angled portion that extends radially outwardly in a distal direction towards the exterior shaft 116. The angled portion can be formed by molding the polymer jacket around a mandrel or by other suitable methods (e.g., a femtosecond laser, drilling, ablation, etc.). An opening 1604 in the shaft 116 can be made by removing a portion of the braid 205 and/or polymer jacket 202 at a location along the shaft 116 corresponding to the desired position of the port 1604. As shown in FIG. 23, the polymer jacket 202 can be heated to soften the polymer 202 and reflow the polymer material so as to smooth the transition between the port 1604 and the lumen 206. Additionally, FIG. 24 is a cross-sectional end view of one embodiment of a shaft 116 having a non-braided portion 1702 reserved for formation of a rapid-exchange port.

Figure 25:
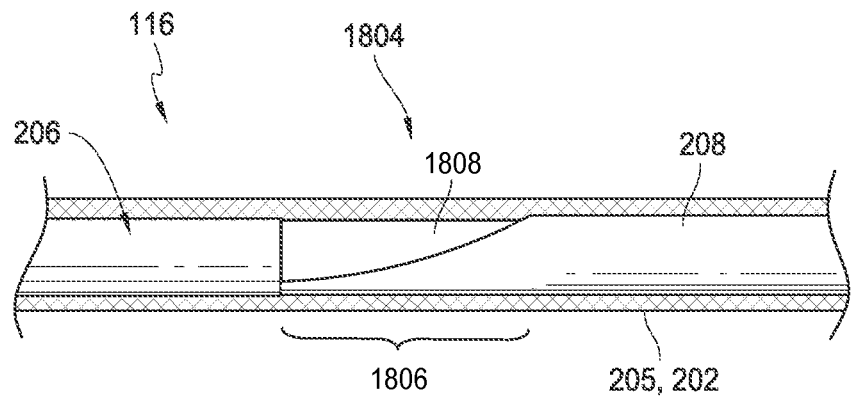
FIG. 25 is a side view of a shaft with a portion of the braid removed for purposes of illustration, the shaft shown during a stage of manufacturing and configured in accordance with an embodiment of the present technology.

FIG. 25 is a side view of a shaft 116 during a stage of manufacturing in accordance with an embodiment of the present technology. As shown in FIG. 25, a proximal portion of the shaft 116 can include an elongated member 208 and a distal portion of the shaft can include a lumen 206. The elongated member 208 can include a tapered distal portion 1806. A polymer fill 1808 can abut a tapering surface of the distal portion 1806 and define the area between the braid/polymer jacket 202, 205, the lumen 206, and distal portion 1806. The polymer fill 1808 can be made of the same polymer used for the polymer jacket 202 and/or a different polymer. A portion of the braid/polymer jacket 205, 202 and a portion of the polymer fill 1808 between the tapering surface can be removed to form the port (generally at location 1804) by ablation, drilling, or other suitable methods.

Figure 26:
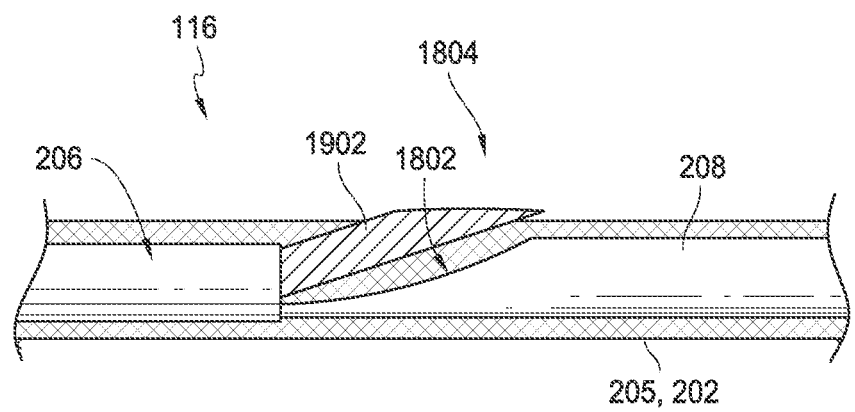
FIG. 26 is a side view of a shaft with a portion of the braid removed for purposes of illustration, the shaft shown during a stage of manufacturing and configured in accordance with an embodiment of the present technology.

FIG. 26 is a side view of a shaft 116 during a stage of manufacturing in accordance with another embodiment of the present technology. The shaft 116 can be generally similar to the shaft 116 described above with reference to FIG. 25, except instead of having a polymer fill 1808, the shaft 116 can include a plug 1902 between the tapering surface and the braid/polymer jacket exterior 202, 205. The plug 1902 can be made of a polymer (dissimilar to that used for the polymer jacket 202) or metal that can be removed once the polymer jacket 202 has been flowed over the braid 205 and set. As such, removal of the plug 1902 forms a newly made opening (generally at location 1804) that is in fluid communication with the lumen 206 at the distal portion of the shaft 116.

Figure 27:
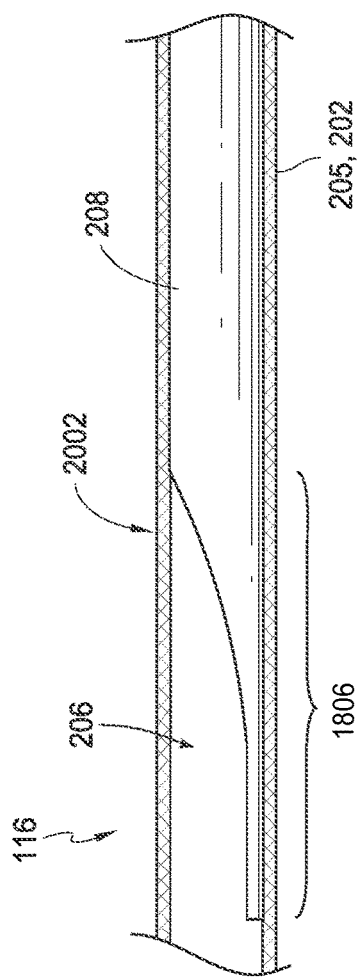
FIG. 27 is a side view of a shaft with a portion of the braid removed for purposes of illustration, the shaft shown during a stage of manufacturing and configured in accordance with an embodiment of the present technology.
Figure 29:
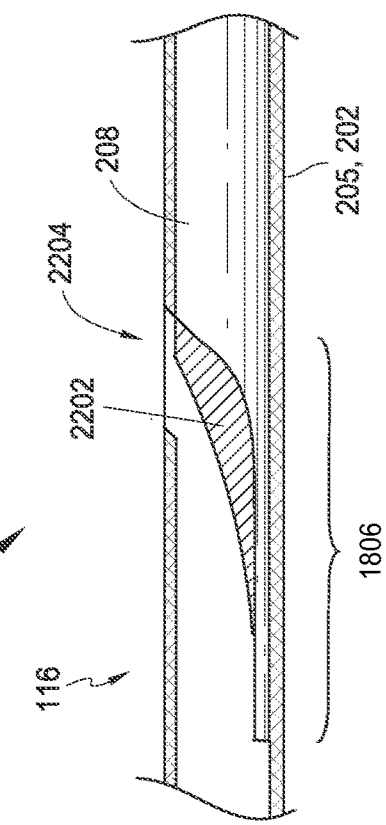
FIG. 29 is a side view of a shaft with a portion of the braid removed for purposes of illustration, the shaft shown during a stage of manufacturing and configured in accordance with an embodiment of the present technology.
Figure 28:
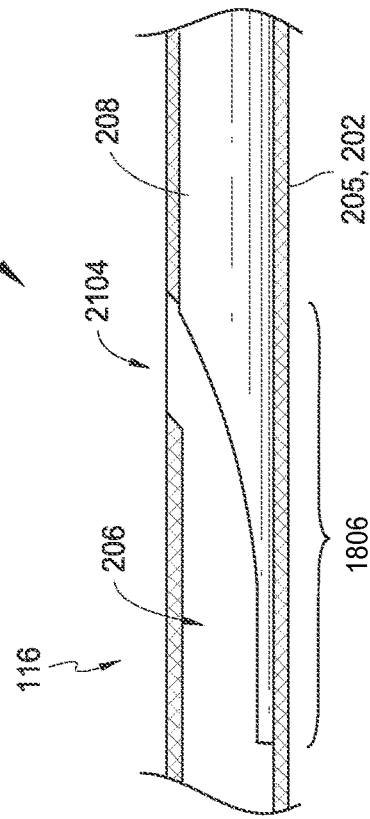
FIG. 28 is a side view of a shaft with a portion of the braid removed for purposes of illustration, the shaft shown during a stage of manufacturing and configured in accordance with an embodiment of the present technology.

FIG. 27 is a side view is a side view of a shaft 116 during a stage of manufacturing configured in accordance with another embodiment of the present technology. As shown in FIG. 27, a proximal portion of the shaft 116 can include an elongated member 208 and a distal portion of the shaft can include a lumen 206. The elongated member 208 can include a tapered distal portion 1806. As shown in FIGS. 27-28, a portion 2002 of the braid/polymer jacket 202, 205 aligned with the tapered distal portion 1806 can be removed create an opening 2104 in the shaft 116 that is in fluid communication with the lumen 206. As shown in FIG. 29, in some embodiments a portion 2202 of the elongated member 208 can also be removed to create a smoother transition to the lumen 206.

Figure 30A:
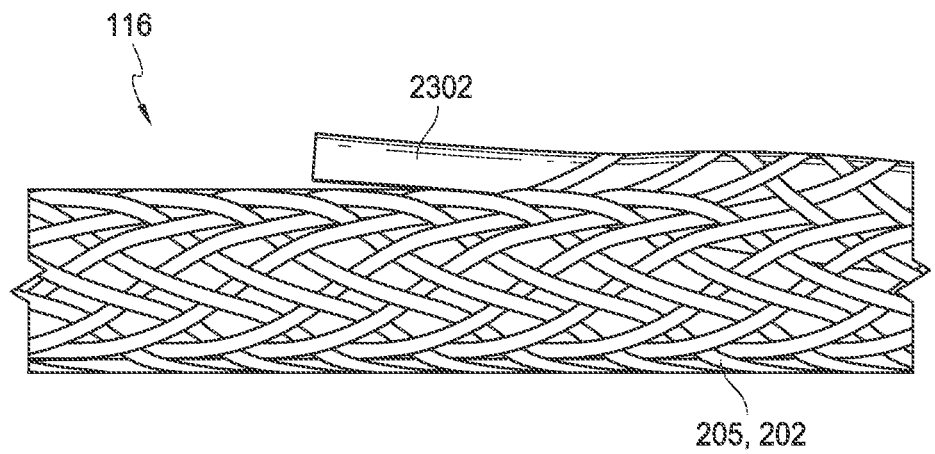
FIG. 30A is a side view of a shaft shown during a stage of manufacturing in accordance with an embodiment of the present technology.
Figure 30B:
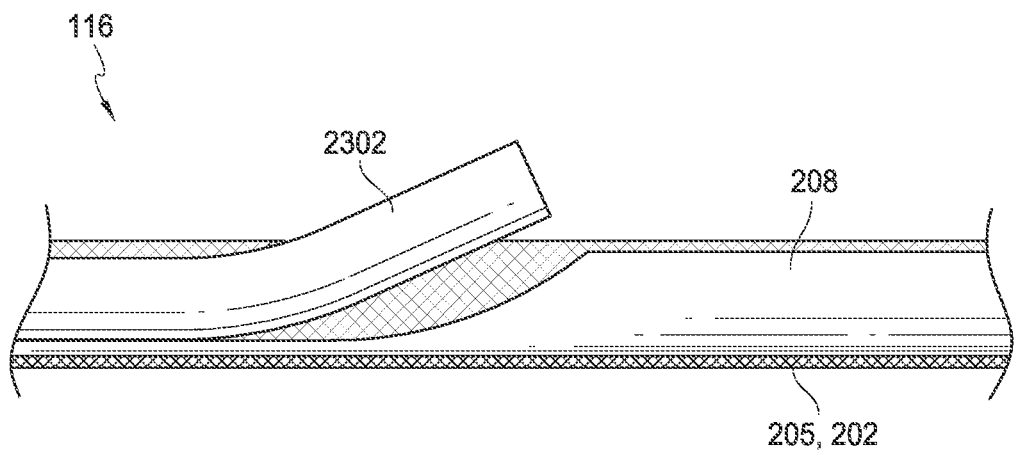
FIG. 30B is a side view of the shaft shown in FIG. 30A with a portion of the braid removed for purposes of illustration.
Figure 31:
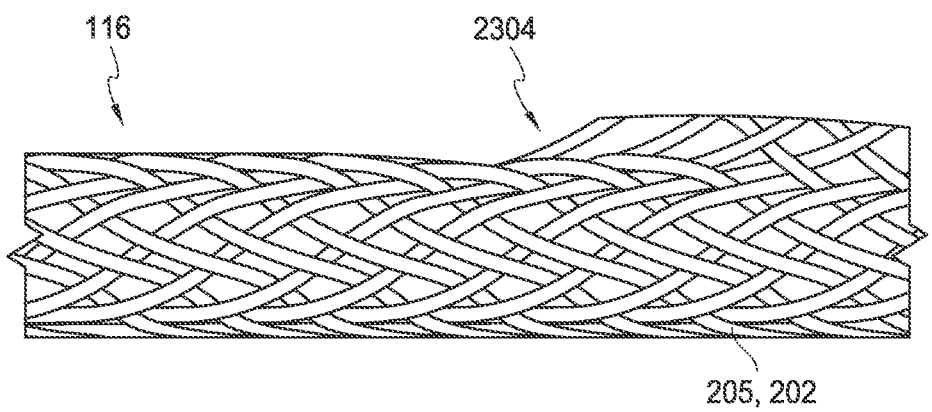
FIG. 31 is a side view of a shaft having a rapid exchange port configured in accordance with an embodiment of the present technology.

FIG. 30A is a side view of a shaft during a stage of manufacturing configured in accordance with the present technology, and FIG. 30B is an opposite side view of the shaft shown in FIG. 30A with a portion of the braid/polymer jacket 205, 202 removed for purposes of illustration. Referring to FIGS. 30A-30B together, during manufacturing the braided portion of the shaft 116 can be formed around an elongated tubular member 2302 (e.g., mandrel, hypotube, etc.) having an angled portion at a distal end. A generally linear portion of the member 2302 can be used to form the central lumen 206 (not shown) at the distal portion 118 of the shaft 116, and the angled portion can form the connection between the lumen 206 (not shown) and the opening 2304 (FIG. 31) at the exterior portion of the shaft 116. As shown in FIG. 31, once the braiding is complete and the polymer set, the member 2302 can be removed to form the opening 2304 configured to be used as a rapid exchange port.

2. Over-the-Wire ("OTW") Embodiments

FIG. 32 shows a catheter shaft 116 configured in accordance with the present technology that is configured to receive a guidewire in an over-the-wire ("OTW") configuration. The shaft 116 can include a braid/polymer exterior 2504 surrounding a first tubular member 208, and a second tubular member 2502. As best shown in the isolated view of the first member 208 in FIG. 33A (and corresponding cross-sectional end views 33B-33D), the first member 208 can have a distal portion 2508 that tapers in the proximal to distal direction for increased flexibility and a smoother transition between the first and second members 208, 2502. A proximal portion of the second member 2502 can be positioned over the at least the distal portion 2508 of the first member 208. As such, the lumen (not shown) of the first member 208 may be contiguous with the lumen (not shown) of the second member 2502. The combined lumens of the first and second members 208, 2502 form a shaft lumen configured to receive a guidewire therethrough.

Figure 34:
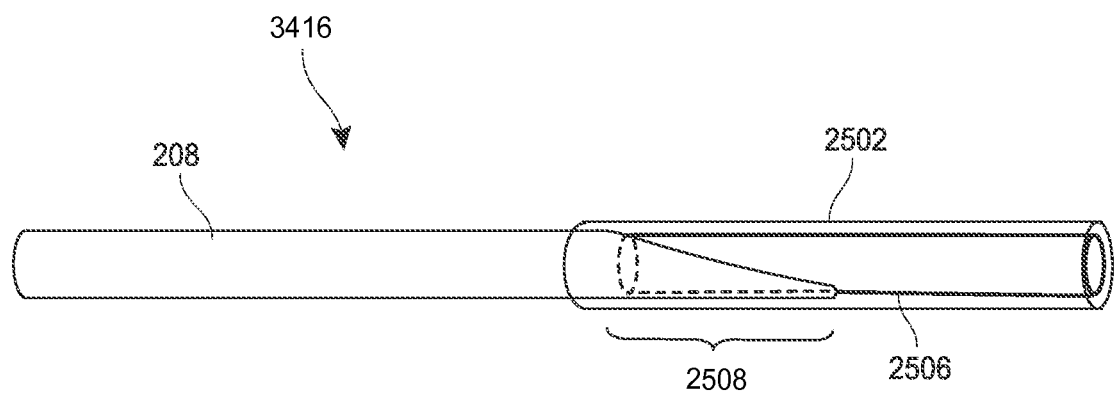
FIG. 34 is a side view of a shaft having an over-the-wire configuration configured in accordance with another embodiment of the present technology.

FIG. 34 shows another embodiment of a catheter shaft 3416 configured in accordance with the present technology that is configured to receive a guidewire in an over-the-wire ("OTW") configuration. The shaft 3416 can be generally similar to the shaft 3416 described above with reference to FIGS. 32-33D, except the shaft 3416 of FIG. 34 includes a third tubular member 2506 positioned within the tapered distal portion 2508 of the first member 208. As such, at least a portion of the third member 2506 is sandwiched between the first member 208 and the second member 2502, thereby providing increased support at the transition between the first and second members 208, 2502. In some embodiments, heat can be applied to the second and third members 2502, 2506 to increase the bond between them.

D. Select Embodiments of Handle Assemblies

Figure 35A:
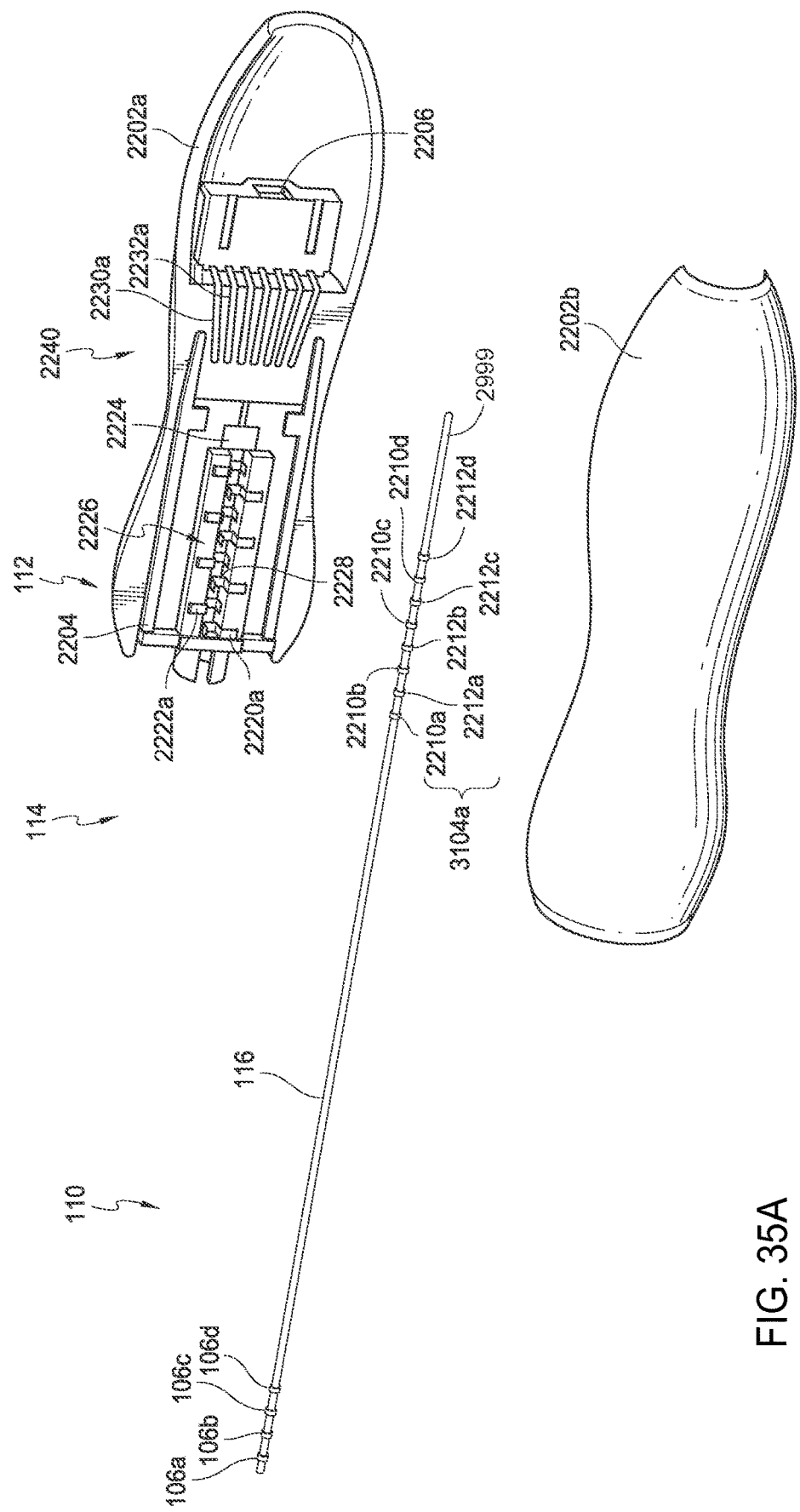
FIG. 35A is a perspective, exploded view of an embodiment of a catheter handle and shaft configured in accordance with the present technology.
Figure 35B:
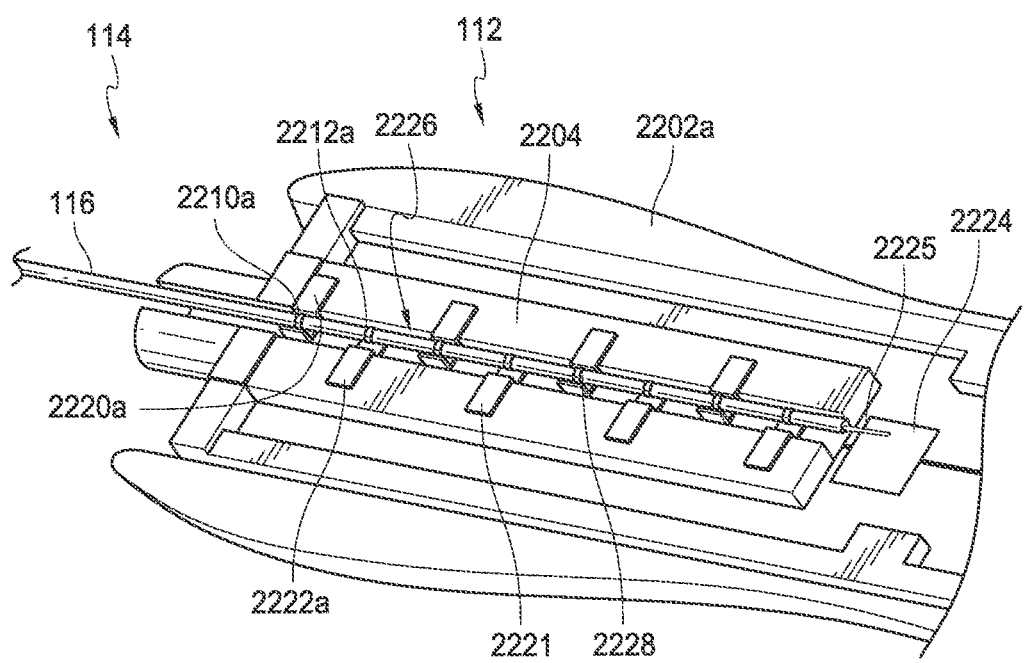
FIG. 35B is a perspective, enlarged view of the proximal portion of the catheter handle shown in FIG. 35A.

FIG. 35A is an exploded, perspective view of the catheter 110 shown in FIG. 1A, and FIG. 35B is an enlarged view of the proximal portion 114 of the shaft 116. Referring to FIGS. 35A and 35B together, a proximal portion 114 of the shaft 116 can be operably coupled to the handle 112 via a snap-fit arrangement. The proximal portion of the shaft 116, for example, may include a plurality of pairs of conductors (referred to as 3104a-d) positioned on an exterior portion of the shaft 116 and electrically coupled to the first and second wires 210, 212 of the TC assemblies 204a-d. For example, the proximal portion 114 of the shaft 116 can include four first conductors 2210 (referred to as conductors 2210a-d) electrically coupled to corresponding first wires 210, and four second conductors (referred to as conductors 2212a-d) electrically coupled to corresponding second wires 212. In other embodiments, the proximal portion 115 can include more or less than eight total conductors depending on the number of electrodes. Furthermore, one conductor (instead of a pair of conductors) could correspond to a pair of first and second wires (e.g., 210a and 212b, etc.). Although in the illustrated embodiment the conductors are shown in an order that corresponds with the electrodes (e.g., distally to proximally, "a" is most distal, "d" is most proximal), in other embodiments the conductors 2210, 2212 can have any order; the order of the conductors 3104a-d does not necessarily correspond to the order of the electrodes 106a-d.

Referring still to FIGS. 35A-35B, the handle 112 includes a housing 2202 including two complimentary halves 2202a and 2202b (only the interior of 2202a shown for ease of description). Each half includes a shaft receiving region 2204, a routing portion 2240, and connector attachment 2206. The shaft receiving region 2204 can include a longitudinal groove 2226 and a plurality of conductive pins 2220a-d and 2222a-d (collectively referred to as 2221), each having a horseshoe-shaped portion 2228 at least partially within the groove 2226. The groove 2226 can be configured to receive the proximal portion 114 of the shaft 116, and the horseshoe-shaped portion 2228 of the pins 2221 can be configured to engage at least a portion of the conductors 2220a, 2210a on the received shaft 116. When the shaft 116 is pressed into place within the groove 2226 of the receiving region 2204 (after aligning the conductors and the pins), the conductors 2220a, 2210a engage the corresponding pin 2220a-d, 2222a-d, thus electrically coupling the shaft 116 to the handle 112. The horseshoe-shaped portion 2228 initially resists the movement of the shaft into the groove; however, past a certain threshold the horseshoe-shaped portion 2228 is forced open and allows the conductor to sit within the horseshoe-shaped portion to securely hold the shaft 116 (e.g., a "snap-fit").

As best seen in FIG. 35B, once the proximal portion 114 of the shaft is in place within the receiving region 2204, the proximal tip 2225 of the shaft can be welded to a plate 2224 mounted within the housing 2202. For example, the braid 205 and polymer jacket 202 can be removed from the proximal tip of the shaft 116 (not shown), thereby exposing the mandrel 2225, which can then be welded to the plate 2224. As such, a proximal portion of the mandrel 2225 can be fixed to an interior portion of the handle 112 to improve the torque response of the shaft 116 (e.g., by reducing and/or preventing axial and rotational movement of the shaft 116 relative to the handle 112).

The conductive pins 2220a-d, 2222a-d can be electrically coupled to the routing portion 2240 (FIG. 35A) that includes a plurality of routing lines 2230a-d, 2232a-d, individually corresponding to the conductive pins 2220a-d, 2222a-d. The routing lines 2230a-d, 2232a-d are coupled to the connector attachment 2206 positioned at a proximal portion of the handle 112, as shown in FIG. 35A. The connector attachment 2206 is configured to be operably coupled with the connector 130 (see FIG. 1A) to electrically connect the handle 112 to the energy generator 132 or other component of the system.

FIG. 36A is a side view of another embodiment of a catheter 2310 configured in accordance with the present technology, and FIG. 36B is an enlarged cross-sectional view of a proximal portion 114 of the handle 2300 shown in FIG. 36A. The catheter 2310 can be generally similar to the catheter 110 described above with reference to FIGS. 1A-1C and 35A-35C except as detailed below. Referring to FIGS. 36A and 36B together, the catheter 2310 can include a handle 2300 having an interior surface with a printed circuit board ("PCB") directly printed thereon. A plurality of routing lines 2318 can extend from the PCB to a recessed receiving region 2320 at the distal end of the handle 2300. The routing lines 2318 can individually correspond to the first wire 210, the second wire 212, and/or the TC assembly 204 (FIG. 1B). A connector 2330 (FIG. 36C) can be coupled to a proximal portion of the PCB board, thereby providing the electrical connection between the handle 2300 and the energy generator 132. As shown in FIG. 36D, a portion of the proximal section of the polymer jacket 2302 can be removed to expose the proximal ends of the TC assemblies 204. As such, the exposed wires 2304 at the proximal portion of the shaft 2316 can be pressed into place in the receiving region, thus electrically coupling the shaft 116 to the handle 112. Moreover, a proximal end of the mandrel 2326 (shown schematically in FIG. 36B) can be fixed to a plate 2322 on the handle 112 to improve the torque response of the shaft 2316. In these and other embodiments, a distal portion 2324 of the handle 112 can be lengthened in a distal direction to improve the torque response of the shaft 2316, as well as increase the surface area available for a user to grip and control the handle 112.

Figure 37A:
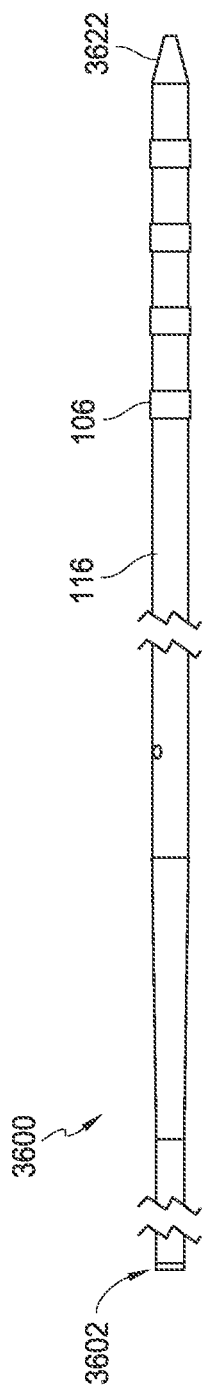
FIG. 37A is a side view of an embodiment of an elongated shaft configured in accordance with the present technology.
Figure 37B:
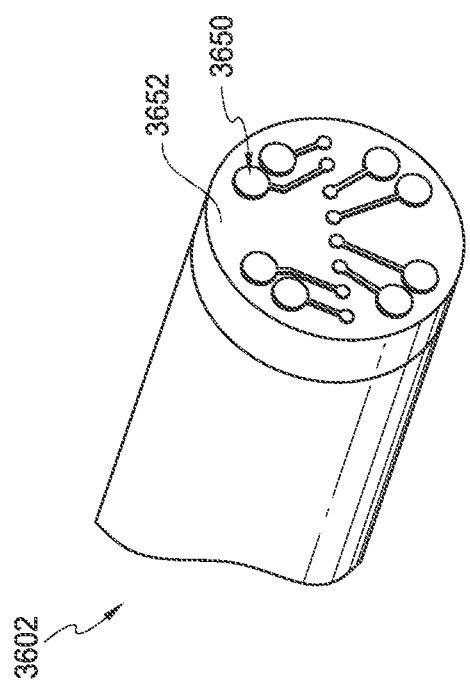
FIG. 37B is a perspective, enlarged view of a proximal portion of the shaft shown in FIG. 37A.

FIG. 37A is a side view of another embodiment of a catheter 3600 configured in accordance with the present technology, and FIG. 37B is an enlarged view of the proximal end of the catheter shaft 116 of the catheter 3600 of FIG. 37A. Referring to FIGS. 37A-37B together, the catheter 3600 can be generally similar to the catheters 110 and 2310 described above with reference to FIGS. 1A-1C, 35A-35C and 36A-36C, except that the catheter 3600 has disc-shaped connector 3652 coupled to the proximal end of the shaft 116. The connector 3652 can be electrically coupled to the TC assemblies (not shown) and provide one or more connection points 3650 at an exterior portion of the disc 3652 that correspond to the TC assemblies. A connector (not shown) can be coupled to the disc 3652 and extend between the shaft 116 and the handle 112 (FIG. 1A) and/or energy generator 132 (FIG. 1A).

III. NEUROMODULATION

Neuromodulation is the partial or complete incapacitation or other effective disruption of nerves innervating, for example, an organ. As an example, renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity. Renal neuromodulation can potentially benefit a variety of organs and bodily structures innervated by sympathetic nerves.

Thermal effects can include both thermal ablation and non-ablative thermal alteration or damage (e.g., via sustained heating and/or resistive heating) to partially or completely disrupt the ability of a nerve to transmit a signal. Desired thermal heating effects, for example, may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for ablative thermal alteration. More specifically, exposure to thermal energy in excess of a body temperature of about 37° C., but below a temperature of about 45° C., may induce thermal alteration via moderate heating of target neural fibers or of vascular structures that perfuse the target fibers. In cases where vascular structures are affected, the target neural fibers may be denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures that perfuse the target fibers. In some patients, it may be desirable to achieve temperatures that thermally ablate the target neural fibers or the vascular structures, but that are less than about 90° C., or less than about 85° C., or less than about 80° C., and/or less than about 75° C. Other embodiments can include heating tissue to a variety of other suitable temperatures. Regardless of the type of heat exposure utilized to induce the thermal neuromodulation, a reduction in renal sympathetic nerve activity (RSNA) is expected.

Various techniques can be used to partially or completely incapacitate neural pathways, such as those innervating the kidneys. The purposeful application of energy (e.g., RF energy, mechanical energy, acoustic energy, electrical energy, thermal energy, etc.) to tissue and/or the purposeful removal of energy (e.g., thermal energy) from tissue can induce one or more desired thermal heating and/or cooling effects on localized regions of the tissue. The tissue, for example, can be tissue of the renal artery and adjacent regions of the renal plexus, which lay intimately within or adjacent to the adventitia of the renal artery. For example, the purposeful application and/or removal of energy can be used to achieve therapeutically effective neuromodulation along all or a portion of the renal plexus.

Many current helical or spiral neuromodulation systems deploy mainly from a distal to proximal direction. Often times the distal end of the electrode array is moveable in a proximal and distal direction but the proximal end of the electrode array is fixed relative to the catheter shaft. As a result, in vessels or portions of vessels with tapered diameters (e.g., the renal artery), many devices first deploy distally where the vessel diameter is smaller, which can prevent the electrodes at the proximal end of the helical structure from making contact with the inner vessel wall. Likewise, achieving contact with the vessel wall along a substantial length of the helical or spiral device can be difficult in vessels with tortuous or unpredictable morphologies. To address this need, the present technology provides several embodiments of devices, systems, and methods that provide bi-directional deployment of a helical or spiral device to better position the electrodes in apposition with the vessel wall.

IV. EXAMPLES

The following examples are illustrative of several embodiments of the present technology:

1. A catheter apparatus, comprising:
   an elongated tubular shaft having a proximal portion and a distal portion, wherein the elongated tubular shaft includes—
   a polymer material;
   a first thermocouple assembly wrapped about and/or embedded within the polymer material of the shaft, wherein the first thermocouple assembly comprises a first pair of wires composed of dissimilar metals;
   a second thermocouple assembly wrapped about and/or embedded within the polymer material of the shaft, wherein the second thermocouple assembly comprises a second pair of wires composed of dissimilar metals, and wherein the second pair of wires is physically and electrically isolated from the first pair of wires along the elongated shaft between the proximal portion and the distal portion;
   a first electrode at the distal portion of the elongated shaft and electrically coupled to the first thermocouple assembly;
   a second electrode at the distal portion of the elongated shaft and electrically coupled to the second thermocouple assembly,
   wherein the distal portion of the shaft and the first and second electrodes together define a therapeutic assembly adapted to be located at a target location within a blood vessel of a human patient,
   wherein the elongated shaft and the therapeutic assembly together define therethrough a guide wire lumen configured to slidably receive a medical guide wire,
   wherein axial movement of the guide wire relative to the therapeutic assembly transforms the therapeutic assembly between (a) a low-profile delivery configuration and (b) a deployed configuration having a spiral shape.

2. The catheter apparatus of example 1, further comprising:
   a third thermocouple assembly helically wrapped about and/or embedded within the polymer material of the shaft, wherein the third thermocouple assembly comprises a third pair of wires;
   a fourth thermocouple assembly helically wrapped about and/or embedded within the polymer material of the shaft, wherein the fourth thermocouple assembly comprises a fourth pair of wires;
   a third electrode at the distal portion of the elongated shaft and electrically coupled to the third thermocouple assembly; and
   a fourth electrode at the distal portion of the elongated shaft and electrically coupled to the fourth thermocouple assembly,
   wherein the first, second, third, and fourth pair of wires are all physically and electrically isolated from each other along the elongated shaft between the proximal portion and the distal portion.

3. The catheter apparatus of example 1 or example 2 wherein the first, second, third, and fourth electrodes comprise gold band electrodes.

4. The catheter apparatus of any of examples 1-3 wherein the individual electrodes are spaced apart from each other along the elongated shaft by 7.5 mm.

5. The catheter apparatus of any of examples 1-4, further comprising a handle that is coupled to the proximal portion of the elongated shaft via a snap fit arrangement.

6. The catheter apparatus of example 5 wherein the proximal portion of the handle comprises four contacts arranged thereon and in electrical contact with corresponding individual wires of the first and second thermocouple assemblies, and wherein the contacts are positioned to mate with corresponding pins carried by the handle when the proximal portion of the shaft is coupled with the handle in a snap fit arrangement.

7. The catheter apparatus of example 6 wherein the contacts are gold contacts.

8. The catheter apparatus of any of examples 1-7, further comprising a rapid exchange port positioned along the shaft between the proximal portion and the distal portion of the shaft and in communication with the guide wire lumen, wherein the portion of the shaft between the rapid exchange port and the proximal portion of the shaft is solid.

9. The catheter apparatus of any of examples 1-8 wherein:
between the rapid exchange port and the distal portion of the shaft, the shaft has a first outer diameter; and
between the rapid exchange port and the proximal portion of the shaft, the shaft has a second outer diameter less than the first outer diameter.

10. The catheter apparatus of any of examples 1-9 wherein the elongated shaft further comprises monofilaments interspersed with the wires of the first and second thermocouple assemblies.

11. The catheter apparatus of any of examples 1-10 wherein the first and/or second thermocouple assemblies have a first pitch at the proximal portion of the shaft and a second pitch at the distal portion of the shaft, wherein the first pitch is less than the second pitch.

12. The catheter apparatus of any of examples 1-11 wherein shaft further includes a braiding element wrapped around the shaft.

13. The catheter apparatus of example 12 wherein the braiding element is intertwined with the first and/or second thermocouple assemblies.

14. A neuromodulation catheter, comprising:
an elongate polymer shaft comprising multiple thermocouple wires arranged thereabout; and
a plurality of neuromodulation elements operably coupled to the polymer shaft at a distal portion of the polymer shaft, wherein individual neuromodulation elements are electrically coupled to corresponding pairs of thermocouple wires,
wherein—
each thermocouple wire is distributed along a helical path extending around a longitudinal axis of the polymer shaft, and wherein the thermocouple wires extending along the polymer shaft are arranged generally parallel with each other, and
at least a portion of the polymer shaft comprises a lumen therethrough sized and shaped to slidably receive a medical guide wire.

15. The neuromodulation catheter of example 14 wherein the polymer shaft comprises four pairs of thermocouple wires arranged thereabout, and wherein the plurality of neuromodulation elements comprises four gold electrodes electrically coupled to corresponding pairs of thermocouple wires.

16. The neuromodulation catheter of example 14 or example 15 wherein the polymer shaft comprises a first region and a second region along the shaft, and wherein the helical path comprises a first pitch throughout the first region, and a second pitch different than the first pitch throughout the second region.

17. The neuromodulation catheter of any of examples 14-16 wherein the distal portion of the polymer shaft is transformable between a low-profile delivery state and an expanded deployed state having a generally helical/spiral configuration.

18. A method of manufacturing a medical device, the method comprising:
positioning a first thermocouple assembly and a second thermocouple assembly about a central mandrel, wherein the first thermocouple assembly comprises a first pair of wires and the second thermocouple assembly comprises a second pair of wires;
braiding the first wires of the first thermocouple assembly and the second wires of the second thermocouple assembly along the mandrel, wherein the first wires and the second wires are spaced apart from each other and arranged in a spiral pattern along the mandrel;
disposing a polymer material over the braided first wires and second wires to form an elongated tubular shaft about the mandrel;
selectively removing portions of the polymer material at a distal region of the elongated shaft to access the first wires of the first thermocouple assembly and the second wires of the second thermocouple assembly;
electrically coupling a first electrode to the exposed portion of the first wires of the first thermocouple assembly;
electrically coupling a second electrode to the exposed portion of the second wires of the second thermocouple assembly; and
removing the mandrel from at least the distal region of the elongated shaft.

19. The method of example 18, further comprising positioning the distal region of the elongated shaft about a mandrel in a spiral configuration after removing the mandrel from at least the distal region, and wherein the method further comprises heat setting the distal region into the spiral shape.

20. The method of example 18 or example 19 wherein:
electrically coupling a first electrode to the exposed portion of the first wires comprises laser welding the first electrode to the individual first wires; and
electrically coupling a second electrode to the exposed portion of the second wires comprises laser welding the second electrode to the individual second wires.

21. The method of any of examples 18-20 wherein the distal region of the elongated shaft comprises a guide wire lumen therethrough, and wherein the method further comprises forming a rapid exchange access port along the elongated shaft and in communication with the guide wire lumen, wherein the rapid exchange access port and the guide wire lumen are sized and shaped to slidably receive a medical guide wire.

22. The method of any of examples 18-21 wherein removing the mandrel from at least the distal region of the elongated shaft comprises removing the mandrel from only the portion of the shaft distal of the rapid exchange access port such the portion of the shaft proximal of the rapid exchange access port is solid therethrough.

VI. CONCLUSION

The above detailed descriptions of embodiments of the present technology are for purposes of illustration only and are not intended to be exhaustive or to limit the present technology to the precise form(s) disclosed above. Various equivalent modifications are possible within the scope of the present technology, as those skilled in the relevant art will recognize. For example, while steps may be presented in a given order, alternative embodiments may perform steps in a different order. The various embodiments described herein and elements thereof may also be combined to provide further embodiments. In some cases, well-known structures and functions have not been shown or described in detail to avoid unnecessarily obscuring the description of embodiments of the present technology.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A catheter apparatus, comprising:
   an elongated tubular shaft having a proximal portion, a distal portion, and a rapid exchange port along the elongated tubular shaft between the proximal portion and the distal portion of the elongated tubular shaft and in communication with a guide wire lumen, wherein a portion of the elongated tubular shaft between the rapid exchange port and the proximal portion of the elongated tubular shaft is solid with no lumen therethrough, and wherein the elongated tubular shaft includes:
   a polymer material;
   a first thermocouple assembly wrapped about the elongated tubular shaft between the proximal portion and the distal portion, wherein the first thermocouple assembly comprises a first pair of wires composed of dissimilar metals;
   a second thermocouple assembly wrapped about the elongated tubular shaft between the proximal portion and the distal portion, wherein the second thermocouple assembly comprises a second pair of wires composed of dissimilar metals, and wherein the second pair of wires is physically and electrically isolated from the first pair of wires along the elongated tubular shaft between the proximal portion and the distal portion;
   a plurality of braiding elements that have different cross-sectional areas and that are intertwined with the first thermocouple assembly and the second thermocouple assembly along a length of the elongated tubular shaft, the plurality of braiding elements being configured to impart a deployed configuration having a spiral shape upon the elongated tubular shaft;
   a first electrode at the distal portion of the elongated tubular shaft and electrically coupled to the first thermocouple assembly; and
   a second electrode at the distal portion of the elongated tubular shaft and electrically coupled to the second thermocouple assembly,
   wherein the first and second electrodes are adapted to be located at a target location within a blood vessel of a human patient,
   wherein the guide wire lumen is configured to slidably receive a medical guide wire,
   wherein axial movement of the medical guide wire transforms the elongated tubular shaft between a low-profile delivery configuration and the deployed configuration having the spiral shape.

2. The catheter apparatus of claim 1, further comprising:
   a third thermocouple assembly helically wrapped about or embedded within the polymer material of the elongated tubular shaft, wherein the third thermocouple assembly comprises a third pair of wires;
   a fourth thermocouple assembly helically wrapped about or embedded within the polymer material of the elongated tubular shaft, wherein the fourth thermocouple assembly comprises a fourth pair of wires;
   a third electrode at the distal portion of the elongated tubular shaft and electrically coupled to the third thermocouple assembly; and
   a fourth electrode at the distal portion of the elongated tubular shaft and electrically coupled to the fourth thermocouple assembly,
   wherein the first, second, third, and fourth pair of wires are all physically and electrically isolated from each other along the elongated tubular shaft between the proximal portion and the distal portion.

3. The catheter apparatus of claim 2 wherein the first, second, third, and fourth electrodes comprise gold band electrodes.

4. The catheter apparatus of claim 2 wherein the first, second, third, and fourth electrodes are each spaced apart from each other along the elongated tubular shaft by 7.5 mm.

5. The catheter apparatus of claim 1, further comprising a handle that is coupled to the proximal portion of the elongated tubular shaft via a snap fit arrangement.

6. The catheter apparatus of claim 5 wherein the handle comprises four contacts in electrical contact with corresponding individual wires of the first and second thermocouple assemblies, and wherein the four contacts are positioned to mate with corresponding pins carried by the handle when the proximal portion of the elongated tubular shaft is coupled with the handle in the snap fit arrangement.

7. The catheter apparatus of claim 6 wherein the four contacts are gold contacts.

8. The catheter apparatus of claim 1 wherein:
   between the rapid exchange port and the distal portion of the elongated tubular shaft, the elongated tubular shaft has a first outer diameter; and between the rapid exchange port and the proximal portion of the elongated tubular shaft, the elongated tubular shaft has a second outer diameter less than the first outer diameter.

9. The catheter apparatus of claim 1 wherein the elongated tubular shaft further comprises monofilaments interspersed with the wires of the first and second thermocouple assemblies.

10. The catheter apparatus of claim 1 wherein the first and second thermocouple assemblies are wrapped about the elongated tubular shaft and have a first pitch at the proximal portion of the elongated tubular shaft and a second pitch at the distal portion of the elongated tubular shaft, and wherein the first pitch is less than the second pitch.

11. A neuromodulation catheter, comprising:
an elongated polymer shaft comprising a first region and a second region along the elongated polymer shaft;
a plurality of thermocouple assemblies each having a pair of thermocouple wires;
a plurality of braiding elements that have different cross-sectional areas and that are intertwined with the plurality of thermocouple assemblies along a length of the elongated polymer shaft, the plurality of braiding elements being configured to impart a deployed configuration having a spiral shape upon the elongated polymer shaft; and
a plurality of neuromodulation elements operably coupled to the elongated polymer shaft at a distal portion of the elongated polymer shaft that includes a lumen therethrough sized and shaped to slidably receive a medical guidewire, wherein each individual neuromodulation is electrically coupled to a corresponding pair of thermocouple wires, wherein:
each thermocouple wire is distributed along a helical path extending around a longitudinal axis of the elongated polymer shaft, wherein the helical path comprises a first pitch throughout the first region, and a second pitch different than the first pitch throughout the second region, and wherein the pairs of thermocouple wires extending along the elongated polymer shaft are arranged generally parallel with each other, and
a portion of the elongated polymer shaft between a proximal portion of the elongated polymer shaft and the distal portion of the elongated polymer shaft being substantially solid throughout its cross-section with no lumen therethrough.

12. The neuromodulation catheter of claim 11 wherein the elongated polymer shaft comprises four pairs of thermocouple wires arranged thereabout, and wherein the plurality of neuromodulation elements comprises four gold electrodes electrically coupled to corresponding pairs of thermocouple wires.

13. The neuromodulation catheter of claim 11 wherein the distal portion of the elongated polymer shaft is transformable between a low-profile delivery state and the deployed configuration having the spiral shape.

* * * * *